(12) United States Patent
Edelson et al.

(10) Patent No.: US 11,410,777 B2
(45) Date of Patent: Aug. 9, 2022

(54) PATIENT RISK EVALUATION

(71) Applicant: THE UNIVERSITY OF CHICAGO, Chicago, IL (US)

(72) Inventors: Dana P. Edelson, Chicago, IL (US); Matthew Churpek, Chicago, IL (US); Robert Gibbons, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 1070 days.

(21) Appl. No.: 14/440,251

(22) PCT Filed: Nov. 1, 2013

(86) PCT No.: PCT/US2013/067992
§ 371 (c)(1),
(2) Date: May 1, 2015

(87) PCT Pub. No.: WO2014/071145
PCT Pub. Date: May 8, 2014

(65) Prior Publication Data
US 2015/0332012 A1 Nov. 19, 2015

Related U.S. Application Data

(60) Provisional application No. 61/731,619, filed on Nov. 30, 2012, provisional application No. 61/721,973, filed on Nov. 2, 2012.

(51) Int. Cl.
*G16H 50/30* (2018.01)
*A61B 5/00* (2006.01)
(Continued)

(52) U.S. Cl.
CPC .......... *G16H 50/30* (2018.01); *A61B 5/7275* (2013.01); *A61B 5/021* (2013.01); *A61B 5/0205* (2013.01)

(58) Field of Classification Search
CPC .......... A61B 2560/0242; A61B 5/0205; A61B 5/02055; G16H 50/30
See application file for complete search history.

(56) References Cited

U.S. PATENT DOCUMENTS

| 5,101,926 A | 4/1992 | Berman et al. ............... 180/272 |
| 7,941,209 B2 | 5/2011 | Hughes et al. ............... 600/523 |

(Continued)

FOREIGN PATENT DOCUMENTS

| GB | 2485243 | 5/2012 |
| WO | WO 2012/140547 | 10/2012 |

OTHER PUBLICATIONS

Nice Guidelines (Year: 2007).*
(Continued)

*Primary Examiner* — Aryan E Weisenfeld
(74) *Attorney, Agent, or Firm* — Norton Rose Fulbright US LLP

(57) ABSTRACT

This disclosure includes various embodiments of apparatuses, systems and methods for evaluating a patient's cardiac risk and/or mental status. Cardiac risk evaluation may be based (e.g., only) on the patient's respiratory rate, heart rate, diastolic blood pressure, age, and/or mental status. An aggregate score, which is indicative likelihood of the patient's cardiac risk, may be calculated based (e.g., only) on the patient's respiratory rate, heart rate, diastolic blood pressure, age, and/or mental status. If the calculated aggregate score exceeds a predetermined threshold, the patient may be identified as having a critical cardiac risk, and actions may be taken to treat the patient. The cardiac risk evaluation may be based further on the patient's mental status, where the patient's mental status may be evaluated based on a game with visual indicators.

35 Claims, 24 Drawing Sheets

(51) Int. Cl.
  A61B 5/0205 (2006.01)
  A61B 5/021 (2006.01)

(56) References Cited

U.S. PATENT DOCUMENTS

| | | | |
|---|---|---|---|
| 8,092,380 B2 | 1/2012 | Rothman et al. | 600/300 |
| 8,100,829 B2 | 1/2012 | Rothman et al. | 600/300 |
| 8,175,895 B2 | 5/2012 | Rosenfeld et al. | 705/3 |
| 8,290,575 B2 | 10/2012 | Tarassenko et al. | 600/512 |
| 8,332,017 B2 | 12/2012 | Senko et al. | 600/509 |
| 8,355,925 B2 | 1/2013 | Rothman et al. | 705/2 |
| 8,403,847 B2 | 3/2013 | Rothman et al. | 600/300 |
| 8,454,506 B2 | 6/2013 | Rothman et al. | 600/300 |
| 2002/0099302 A1* | 7/2002 | Bardy | A61B 5/0002 600/510 |
| 2003/0073885 A1 | 4/2003 | Theodoracopulos et al. | 600/300 |
| 2008/0235049 A1 | 9/2008 | Morita et al. | 705/2 |
| 2009/0093686 A1 | 4/2009 | Hu et al. | 600/300 |
| 2009/0105550 A1* | 4/2009 | Rothman | G06Q 50/22 600/300 |
| 2009/0216556 A1 | 8/2009 | Martin et al. | 705/3 |
| 2009/0281398 A1 | 11/2009 | Hogan | 600/301 |
| 2010/0221187 A1* | 9/2010 | Lieberburg | C07K 16/18 424/9.2 |
| 2011/0068935 A1 | 3/2011 | Riley et al. | 340/575 |
| 2011/0184250 A1 | 7/2011 | Schmidt et al. | 600/300 |
| 2013/0211858 A1 | 8/2013 | Ohnemus et al. | 705/3 |
| 2013/0232103 A1 | 9/2013 | Saeed | 706/46 |
| 2013/0290231 A1 | 10/2013 | Chbat | 706/21 |

OTHER PUBLICATIONS

Nice Guidelines Date (Year: 2007).*
Yiu (Year: 2019).*
Sicotte (Year: 2018).*
Townley, Both blood pressure numbers may predict heart disease, https://www.medicalnewstoday.com/articles/325861 (Year: 2019).*
Lee, Cardiovascular Risk of Isolated Systolic or Diastolic Hypertension in Young Adults, https://www.ahajournals.org/doi/10.1161/CIRCULATIONAHA.119.044838 (Year: 2020).*
Haider, Systolic blood pressure, diastolic blood pressure, and pulse pressure as predictors of risk for congestive heart failure in the Framingham Heart Study, https://pubmed.ncbi.nlm.nih.gov/12513039/ (Year: 2003).*
Lichtenstein, Systolic and diastolic blood pressures as predictors of coronary heart disease mortality in the Whitehall study, https://www.ncbi.nlm.nih.gov/pmc/articles/PMC1416862/ (Year: 1985).*
Berlot G, Pangher A, Petrucci L, Bussani R, Lucangelo U. Anticipating events of in-hospital cardiac arrest. Eur J Emerg Med. 2004;11(1):24-8.
Bleyer AJ, Vidya S, Russell GB, Jones CM, Sujata L, Daeihagh P, et al. Longitudinal analysis of one million vital signs in patients in an academic medical center. Resuscitation. 2011; 82(11): 1387-92.
Churpek et al. "Using Electronic Health Record Data to Develop and Validate a Prediction Model for Adverse Outcomes on the Wards" *Chest.* 2012.
Churpek MM, Yuen TC, Huber MT, Park SY, Hall JB, Edelson DP. Predicting cardiac arrest on the wards: a nested case-control study. Chest. 2012; 141 (5): 1170-6.
Churpek MM, Yuen TC, Park SY, Meltzer DO, Hall JB, Edelson DP. Derivation of a cardiac arrest prediction model using ward vital signs*. Crit Care Med. 2012; 40(7):21 02-8.
Cretikos M, Chen J, Hillman K, Bellomo R, Finfer S, Flabouris A, et al. The objective medical emergency team activation criteria: a case-control study. Resuscitation. 2007;73(1):62-72.
Cuthbertson BH, Boroujerdi M, McKie L, Aucott L, Prescott G. Can physiological variables and early warning scoring systems allow early recognition of the deteriorating surgical patient? Crit Care Med. 2007; 35(2):402-9.
Cuthbertson BH, Boroujerdi M, Prescott G. The use of combined physiological parameters in the early recognition of the deteriorating acute medical patient. J R Coll Physicians Edinb. 2010; 40(1):19-25.
Edelson DP, Litzinger B, Arora V, Walsh D, Kim S, Lauderdale DS, et al. Improving in-hospital cardiac arrest process and outcomes with performance debriefing. Arch Intern Med. 2008; 168(10):1063-9.
Edelson et al. "Abstract P92: Provider Intuition Predicts Clinical Deterioration in Ward Patients" Resuscitation Science Symposium. 2012.
Edelson, MD, MS et al. "Patient Acuity Rating: Quantifying Clinical Judgment Regarding Inpatient Stability" *Journal of Hospital Medicine.* vol. 6 No.8, Oct. 2011,.
Edelson, MD, MS. "A Novel Mental Status Evaluation Tool" *Mental Status,* 2012.
Edelson, MD, MS. Diagnosing Mental Status Changes in the Hospital, Power Point Presentation, Presented Nov. 22, 2011.
Edelson, MD. "Chicago Rating for Unstable Medical Patients (CRUMP) Index Detailed Protocol Narrative" 2007.
Efron B. Logistic-Regression, Survival Analysis, and the Kaplan-Meier Curve. Journal of the American Statistical Association. 1988; 83(402):414-25.
Escobar GJ, LaGuardia JC, Turk BJ, Ragins A, Kipnis P, Draper D. Early detection of impending physiologic deterioration among patients who are not in intensive care: development of predictive models using data from an automated electronic medical record. J Hosp Med. 2012; 7(5):388-95.
Excellence: NifHaC. Acutely ill patients in hospital: recognition of and response to acute illness in adults in hospital. NICE clinical guideline No. 50. London. 2007.
Fine MJ, Auble TE, Yealy DM, Hanusa BH, Weissfeld LA, Singer DE, et al. A prediction rule to identify low-risk patients with community-acquired pneumonia. N Engl J Med. 1997; 336(4):243-50.
Gibbons RD, Duan N, Meltzer D, Pope A, Penhoet ED, Dubler NN, et al. Waiting for organ transplantation: results of an analysis by an Institute of Medicine Committee. Biostatistics. 2003; 4(2):207-22.
Hillman K, Chen J, Cretikos M, Bellomo R, Brown D, Doig G, et al. Introduction of the medical emergency team (MET) system: a cluster-randomised controlled trial. Lancet. 2005; 365(9477):2091-7.
Hodgetts TJ, Kenward G, Vlachonikolis IG, Payne S, Castle N. The identification of risk factors for cardiac arrest and formulation of activation criteria to alert a medical emergency team. Resuscitation. 2002; 54(2): 125-31.
Humes and Floyd. "Measures of Working Memory, Sequence Learning, and Speech Recognition in the Elderly" *Journal of Speech, Language, and Hearing Research,* vol. 48, p. 224-235, Feb. 2005,.
Ingram DD, Kleinman JC. Empirical Comparisons of Proportional Hazards and Logistic-Regression Models. Statistics in Medicine. 1989;8(5):525-38.
International Search Report for PCT/US2013/67992, mailed on Mar. 28, 2014.
Jenkins PF, Thompson CH, Barton LL, Jenkins PF, Thompson CH, Barton LL. Clinical deterioration in the condition of patients with acute medical illness in Australian hospitals: improving detection and response. Medical Journal of Australia. 2011; 194(11):596-8.
Kellett J, Kim A. Validation of an abbreviated Vitalpac Early Warning Score (ViEWS) in 75,419 consecutive admissions to a Canadian regional hospital. Resuscitation. 2012;83(3):297-302.
Knaus WA, Draper EA, Wagner DP, Zimmerman JE. Apache II: a severity of disease classification system. CritCare Med. 1985;13(10):818-29.
Marshall SD, Kitto S, Shearer W, Wilson SJ, Finnigan MA, Sturgess T, et al. Why don't hospital staff activate the rapid response system (RRS)? How frequently is it needed and can the process be improved? Implement Sci. 2011; 6:39.
Meadow et al. "Serial Assessment of Mortality in the Neonatal Intensive Care Unit by Algorithm and Intuition: Certainty, Uncertainty, and Informed Consent" American Academy of Pediatrics. 109 p. 878-886, 2002.

(56) References Cited

OTHER PUBLICATIONS

Merchant RM, Yang L,,Becker LB, Berg RA, Nadkarni V, Nichol G, et al. Incidence Of treated cardiac arrest in hospitalized patients in the United States. Crit Care Med. 2011;39:2401-2406.

Moore and Staum. "Effects of Age and Nationality on Auditory/Visual Sequential Memory of English and American Children" Bulletin of the Council for Research in Music Education, No. 91, Eleventh edition, pp. 126-131, 1987.

Prytherch DR, Smith GB, Schmidt P, Featherstone PI, Stewart K, Knight D, et al. Calculating early warning scores—a classroom comparison of pen and paper and hand-held computer methods. Resuscitation. 2006; 70(2): 173-8.

Prytherch DR, Smith GB, Schmidt PE, Featherstone PL ViEWS-Towards a national early warning score for detecting adult inpatient deterioration. Resuscitation. 2010; 81(8):932-7.

Quant HC "Executive Summary" Mar. 30, 2012.

Ranson JH, Rifkind KM, Roses DF, Fink SD, Eng K, Spencer FC. Prognostic signs and the role of operative management in acute pancreatitis. Surg Gynecol Obstet. 1974; 139(1):69-81.

Smith GB, Prytherch DR, Schmidt PE, Featherstone PI, Higgins B. A review, and performance evaluation, of single-parameter "track and trigger" systems. Resuscitation. 2008; 79(1): 11-21.

Smith GB, Prytherch DR, Schmidt PE, Featherstone PL Review and performance evaluation of aggregate weighted 'track and trigger' systems. Resuscitation. 2008; 77(2): 170-9.

Steyerberg EW, Harrell FE, Jr., Borsboom GJ, Eijkemans MJ, Vergouwe Y, Habbema JD. Internal validation of predictive models: efficiency of some procedures for logistic regression analysis. J Clin Epidemiol. 2001;54(8):774-81.

Subbe CP, Gao H, Harrison DA. Reproducibility of physiological track-and-trigger warning systems for identifying at-risk patients on the ward. Intensive Care Med. 2007; 33(4):619-24.

Subbe CP. Better ViEWS ahead? It is high time to improve patient safety by standardizing Early Warning Scores, Resuscitation. 2010; 81(8):923-4.

Zekveld et al., "The Relationship Between Nonverbal Cognitive Functions and Hearing Loss" *Journal of Speech, Language, and Hearing Research*. vol. 50 pp. 74-82, Feb. 2007.

\* cited by examiner

What month is it? ~334

- November
- March
- September
- July
- August

FIG. 3J

What day is it? ~336

- Sunday
- Thursday
- Saturday
- Monday
- Friday

FIG. 3K

| Score | 3 | 2 | 1 | 0 | 1 | 2 | 3 |
|---|---|---|---|---|---|---|---|
| Respiratory rate | | ≤8 | | 9-14 | 15-20 | 21-29 | >29 |
| Heart rate | ≤40 | 41-50 | 51-100 | | 101-110 | 111-129 | >129 |
| Systolic BP | ≤70 | 71-80 | 81-100 | 101-199 | | ≥200 | |
| Temperature | | ≤35 | 35.1-36 | 36.1-38 | 38.1-38.5 | ≥38.6 | |
| Neurological | | | | Alert | Voice | Pain | Unresp |

FIG. 9
(Prior Art)

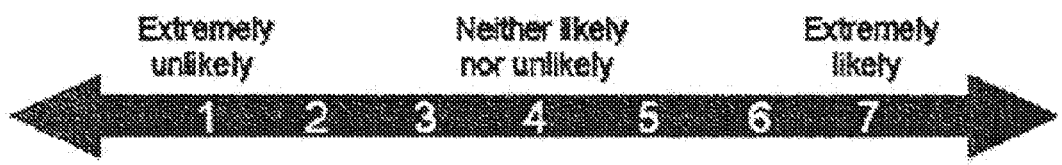

FIG. 12

| Patient and Admission Characteristics | | | |
|---|---|---|---|
| Characteristic | General Medicine Teaching Services | Multispecialty Non-Teaching Services | P-Value |
| Patients (n) | 1,373 | 290 | NA |
| Admissions (n) | 1,660 | 353 | NA |
| Age, mean (SD) years | 57 (21) | 57 (13) | 0.73 |
| Women, n (%) | 1,006 (61) | 173 (48) | <0.001 |
| Race, n (%) | | | <0.001 |
|   White | 203 (12) | 133 (37) | |
|   Black | 1,129 (68) | 125 (35) | |
|   Hispanic | 26 (2) | 34 (9) | |
|   Asian | 11 (1) | 10 (3) | |
|   Other/unknown | 291 (18) | 57 (16) | |
| Severity of illness, n (%) | | | <0.001 |
|   Minor | 121 (7) | 2 (1) | |
|   Moderate | 461 (28) | 44 (12) | |
|   Major | 677 (41) | 179 (50) | |
|   Extreme | 329 (20) | 123 (34) | |
|   N/A | 77 (4) | 11 (3) | |
| Discharged home, n (%) | 1,347 (81) | 282 (79) | 0.25 |
| Expired (not hospice), n (%) | 25 (2) | 28 (8) | <0.001 |

Abbreviation: N/A, not applicable.

FIG. 13

| Weighted Kappa Statistics by Provider Pair | | | |
|---|---|---|---|
| Provider Pair | Observations (n) | Agreement (%) | Weighted Kappa |
| Interns vs residents | 1,006 | 87.1 | 0.42 |
| Residents vs attendings | 1,012 | 82.5 | 0.35 |
| Interns vs attendings | 1,026 | 84.4 | 0.32 |
| Midlevels vs attendings | 208 | 85.0 | 0.43 |

FIG. 14

| Patient Acuity Rating (PAR) Sensitivities and Specificities | | | | |
|---|---|---|---|---|
| PAR | All Patients (n) | Decompensating Patients (n) | Sensitivity (%) | Specificity (%) |
| 7 | 40 | 12 | 16.2 | 99.2 |
| $\geq 6$ | 184 | 30 | 40.5 | 95.4 |
| $\geq 5$ | 561 | 46 | 62.2 | 84.6 |
| $\geq 4$ | 1,120 | 61 | 82.4 | 68.3 |
| $\geq 3$ | 2,044 | 69 | 93.2 | 41.0 |
| $\geq 2$ | 3,005 | 73 | 98.6 | 12.3 |
| $\geq 1$ | 3,419 | 74 | 100.0 | 0.0 |

FIG. 15

Area Under the Patient Acuity Rating (PAR) Receiver Operator Characteristics Curve by Provider

| Service | Provider | Observations (n) | PAR, median (IQR) | AUROC (95% CI) |
|---|---|---|---|---|
| General medicine | Interns | 1,567 | 3 (2-4) | 0.79 (0.70, 0.88) |
| General medicine | Residents | 1,611 | 3 (2-4) | 0.69 (0.59, 0.78)* |
| General medicine | Attendings | 1,791 | 3 (2-4) | 0.84 (0.78, 0.90)* |
| Multispecialty | Attendings | 823 | 3 (2-4) | 0.88 (0.79, 0.97) |
| Multispecialty | Midlevels | 242 | 3 (2-4) | 0.80 (0.64, 0.95) |
| Combined | All | 3,419 | 3 (2-4) | 0.82 (0.77, 0.87) |

Abbreviations: AUROC, area under the receiver operator characteristics curve; CI, confidence interval; IQR, interquartile range.
* The only significant difference in pair-wise comparison occurred between residents and attendings (P = 0.01).

FIG. 16

PATIENT RISK EVALUATION

CROSS-REFERENCE TO RELATED APPLICATIONS

This application is a national phase application under 35 U.S.C. § 371 of International Application No. PCT/US2013/067992, filed Nov. 1, 2013, which claims benefit of priority to U.S. Provisional Patent Application No. 61/731,619 to Dana P. Edelson et al. filed Nov. 30, 2012 and entitled "Patient Risk Evaluation," and claims benefit of priority to U.S. Provisional Patent Application No. 61/721,973 to Dana P. Edelson et al. filed Nov. 2, 2012 and entitled "Patient Risk Evaluation,". The entire contents of each of the above-referenced disclosures are specifically incorporated herein by reference without disclaimer.

STATEMENT REGARDING FEDERALLY SPONSORED RESEARCH

This invention was made with government support under grant Nos. HL097157 and HL007605 awarded by the National Institutes of Health (NIH). The government has certain rights in the invention.

BACKGROUND

1. Field of the Invention

This invention relates generally to predictive risk evaluation for patients, and more particularly, but not by way of limitation, to evaluating a (e.g., hospitalized) patient's clinical risk based on quantitative indications of a variety of factors (e.g., a patient's respiratory rate, heart rate, diastolic blood pressure, demographics (e.g., age), and/or laboratory data (e.g., potassium, anion gap, platelet count)).

2. Description of Related Art

Approximately 200,000 in-hospital cardiac arrests (CAs) occur in the United States each year, and only 20% of these patients survive to discharge. Despite decades of research, this dismal survival rate has changed little. There is evidence that many CAs may be preventable and that warning signs such as abnormal vital signs occur hours before the event. This evidence led to the development of rapid response teams (RRTs), a multidisciplinary group of trained caregivers who bring critical care resources to deteriorating patients on the hospital wards. Despite the common sense nature of this type of intervention, clinical trials have failed to demonstrate a consistent improvement in hospital-wide CA rates or mortality.

Adverse events on hospital wards, such as cardiac arrest and death, are rarely sudden and are often heralded by abnormal vital signs hours before the event. However, these signs are often missed or not acted on appropriately, even in hospitals with mature rapid response systems. In 2007, the National Institute for Health and Clinical Excellence recommended that physiological track and trigger systems should be used to monitor all adult patients in acute hospital settings. These systems, also known as early warning scores, typically use vital sign thresholds to identify at-risk patients. Currently there are over 100 different published track and trigger systems, most of which are hospital-specific modifications of the original Early Warning Score, developed using expert opinion, and have demonstrated variable levels of reliability, validity, and utility. In the past few years, there has been a move toward scientifically derived risk scores and unifying the criteria across hospitals in some countries.

Physiologic track and trigger systems are often divided into single parameter, multiple parameter, and aggregate weighted systems, and there have been recent developments in each of these categories.

A single parameter system generally includes a list of individual physiologic criteria that, if reached by a particular patient, triggers a response. Since any one abnormality on the list may trigger the response, these systems are the easiest to implement, requiring no score calculation. The first such system is believed to have been developed in the early 1990's in Liverpool, Australia and included vital signs, laboratory values, and specific conditions such as new arrhythmia and amniotic fluid embolism. The Medical Early Response Intervention and Therapy (MERIT) trial used a variation of these criteria, and it remains the most commonly described of the single parameter tools today. Both of these early systems were developed using expert opinion rather than being statistically derived based on ward vital signs. A test of the MERIT system constitutes the only multicenter randomized trial of RRTs. The results indicate that the criteria used to activate the RRT had a sensitivity and specificity of less than 50% for CA, intensive care unit (ICU) transfer, or death. In addition, when present, the activation criteria triggered the RRT less than 15 minutes before the adverse event in most cases. However, recently Cretikos and colleagues used a case-control design to develop an evidence-based modification to the MERIT criteria using data from the control arm of the trial. This model (respiratory rate ≥28 breaths per minute, heart rate ≥140 beats per minute, systolic blood pressure ≤85 mm Hg, or a decrease in Glasgow Coma Scale score of >2 points), had a sensitivity of 59.6% and specificity of 93.7% for predicting the composite outcome of cardiac arrest, death, or ICU transfer, compared to 50.4% sensitivity and 93.3% specificity.

Multiple-variable or multiple-parameter systems have also been developed, which use combinations of different physiologic criteria, generally without calculation of a score, to activate a rapid response system. Instead, these systems generally involve assigning cutoffs to vital signs and determining combinations that are predictive of negative health events. These scores allow for stratification of patient risk without development of an algorithm. These systems are the least-commonly described but have the advantage of allowing for risk stratification and a graded response, without requiring a complex calculation. A recent example of this type of system was developed by Bleyer and colleagues using vital sign cut-offs that were individually associated with at least 5% in-hospital mortality. The critical values they identified were a systolic blood pressure of <85 mm Hg, heart rate of >120 beats per minute, temperature of <35° or >38.9° Celsius, oxygen saturation of <91%, respiratory rate of <13 or of >23 breaths per minute, and level of consciousness recorded as anything but "alert." They assigned one point for each critical value and found that having three simultaneous critical values was associated with 23.6% in-hospital mortality. In addition, the authors compared their score to two aggregate weighted risk scores, the Modified Early Warning Score (MEWS) (Table A) and the Vital-PAC™ Early Warning Score (ViEWS) (Table B) and found similar accuracy for detecting in-hospital mortality (areas under the receiver operating characteristic curves (AUCs) of 0.85, 0.87, and 0.86, respectively).

TABLE A

Modified early warning score (MEWS)

| Score | 3 | 2 | 1 | 0 | 1 | 2 | 3 |
|---|---|---|---|---|---|---|---|
| Respiratory rate | | <9 | | 9-14 | 15-20 | 21-29 | >29 |
| Heart rate | | <40 | 41-50 | 51-100 | 101-110 | 111-129 | >129 |
| Systolic BP | <70 | 71-80 | 81-100 | 101-199 | | >199 | |
| Temperature | | <35 | | 35-38.4 | | >38.4 | |
| Neurological | | | | Alert | Voice | Pain | Unresp |

*Abbreviations: BP, blood pressure; Unresp, unresponsive

TABLE B

VitalPAC™ early warning score (ViEWS)

| Score | 3 | 2 | 1 | 0 | 1 | 2 | 3 |
|---|---|---|---|---|---|---|---|
| Respiratory rate | <9 | | 9-11 | 12-20 | | 21-24 | >24 |
| Oxygen saturation | <92 | 92-93 | 94-95 | 96-100 | | | |
| Supplemental oxygen use | | | | No | | | Yes (any O2) |
| Heart rate | | <41 | 41-50 | 51-90 | 91-110 | 111-130 | >130 |
| Systolic BP | <91 | 91-100 | 101-110 | 111-249 | >249 | | |
| Temperature | <35.1 | | 35.1-36 | 36.1-38 | 38.1-39 | >39 | |
| Neurological | | | | Alert | | | Voice Pain Unresp |

*Abbreviations: BP, blood pressure; Unresp, unresponsive

The most complex systems developed to activate RRTs are believed to generally fall under the category of aggregate weighted scoring systems. In general, these scoring systems categorize vital signs and other variables into different degrees of physiologic abnormality and then assign point values to each category. The systems allow for patient risk stratification, but can be error prone when calculated manually. Examples of these systems include the Early Warning Score (EWS) and its variations (generally based on expert opinion), including MEWS and Standardized Early Warning Score (SEWS) (Table C), as well as the ViEWS, which adds variables not utilized by the MEWS or SEWS.

TABLE C

Standardized early warning score (SEWS)

| Score | 3 | 2 | 1 | 0 | 1 | 2 | 3 |
|---|---|---|---|---|---|---|---|
| Respiratory rate | <9 | | | 9-20 | 21-30 | 31-35 | >35 |
| Oxygen saturation | <85 | 85-89 | 90-92 | 93-100 | | | |
| Heart rate | <30 | 30-39 | 40-49 | 50-99 | 100-109 | 110-129 | >129 |
| Systolic BP | <70 | 70-79 | 80-99 | 100-199 | | >199 | |
| Temperature | <34 | 34-34.9 | 35-35.9 | 36-37.9 | 38-38.9 | >38.9 | |
| Neurological | | | | Alert | Voice | Pain | Unresp |

*Abbreviations: BP, blood pressure; Unresp, unresponsive

The ViEWS is one of the most recently developed aggregate weighted risk scores. ViEWS is similar to previously published early warning scores, and includes heart rate, respiratory rate, temperature and systolic blood pressure but adds oxygen saturation and the use of supplemental oxygen (Table B). In one study, the weighting for different vital sign abnormalities was adjusted based on the investigators' analyses, prior literature, and trial and error. And a study in the dataset from which the ViEWS was derived found that it outperformed 33 other risk scores in a cohort of 35,585 acute medical patients for the outcome of death within 24 hours of a ward vital sign set. Further, an abbreviated ViEWS, without mental status, was externally validated in a separate study in a Canadian hospital, where it was found to have an AUC of 0.93 for mortality and 0.72 for ICU transfer within 48 hours using admission vital sign data.

Another aggregate weighted scoring system was developed by Tarassenko and colleagues using continuous vital sign data in high-risk patients on the wards or step-down units. They derived a scoring system based on the distributions of respiratory rate, heart rate, systolic blood pressure, and oxygen saturation in their dataset. Although they did not evaluate the accuracy of their system for detecting adverse outcomes, they are currently conducting a clinical trial using their system on the trauma wards at a teaching hospital.

There are several other recent additions to the literature. These include the Worthing physiological scoring system, which was statistically derived using admission data. When applied to a validation dataset, the system had an AUC of 0.72 for the outcome of in-hospital mortality. A disadvantage of this system is that it requires the measurement of oxygen saturation on room air, which is not always collected. In addition, a form of the MEWS was recently introduced in the Netherlands that includes nurse worry and urine output, and was validated in a population of surgical patients using the highest score achieved for each patient during that hospitalization. A score of 3 or more had a sensitivity of 74% and specificity of 82% for a composite outcome that included mortality, ICU transfer, and severe surgical complications. In another study, Kho and colleagues developed a risk score by altering the vital sign weightings in the MEWS, adding body mass index and age, and removing mental status, based on prior literature and a review of calls to their hospital's RRT. Using the maximum score for each patient on the wards, their model had an AUC of 0.72 for the combined outcome of code team activation, cardiac arrest, or ICU transfer. In addition, Cuthbertson and colleagues used discriminant function analysis in two case-control studies, one in medical and another in surgical patients. They utilized the highest, lowest, and median vital sign values for patients in the 48-hour period before transfer to the ICU (cases) or to a lower acuity unit (controls). The resulting models were at least as accurate as the other published risk scores they compared their models to in both studies.

Finally, using electronic medical record data, investigators from Kaiser Permanente developed a 24 variable model that included vital signs, laboratory values, severity of illness scores and longitudinal chronic illness burden scores. Their model had an AUC of 0.78 in a validation dataset for detecting a combined end-point of ICU transfer or death outside the ICU. The accuracy of the system has strong implications for long term success, both in terms of identifying more cases (i.e. sensitivity) to minimize adverse events and preventing false alarms (i.e. specificity) to minimize resource expenditure and alarm fatigue. For example, consider a hospital that has 20,000 admissions per year and 1000 events (ICU transfers, deaths, and ward cardiac arrests). An improvement in sensitivity of 5%, at the same specificity level, would result in the detection of an additional 50 adverse events per year (1000 events multiplied by the difference in sensitivity of 5%). In addition, an improvement in specificity of 5%, at the same level of sensitivity, would result in 950 fewer "false-alarms" per year (19,000 admissions who did not experience the event multiplied by the difference in specificity of 5%). Multiplying these results over many hospitals across the country would result in a considerable public health benefit, and illustrates the importance of efforts to improve the accuracy of early warning scores.

Studies investigating the accuracy of published activation criteria found a wide range of sensitivities and specificities. The implementation of RRT activation systems with poor accuracy results in critically ill patients remaining on the wards without needed interventions and an overburdened system due to a high rate of false alarms. Development of an accurate prediction tool to detect critically ill patients on the wards could improve identification of at-risk patients and decrease false-positives that lead to alarm-fatigue and increase healthcare costs.

SUMMARY

Embodiments of apparatuses, systems and methods for evaluating a (e.g., hospitalized) patient's clinical risk for deterioration and/or mental status are disclosed. The risk evaluation may be based on the patient's vital signs including, for example, respiratory rate, heart rate, diastolic blood pressure, demographics (e.g., age), and/or laboratory data (e.g., potassium, anion gap, platelet count). An aggregate score, which is indicative of the likelihood of the patient's cardiac risk, may be calculated based on the patient's respiratory rate, heart rate, diastolic blood pressure, and age. An aggregate score, which is indicative of the likelihood of the patient's cardiac risk, may be calculated based on the patient's respiratory rate, heart rate, diastolic blood pressure, age, prior ICU stay, temperature, the use of in-room oxygen, the BUN measurement, the anion gap, hemoglobin, platelet count, and white blood cell count. An aggregate score, which is indicative of the likelihood of the patient's imminent need to transfer to the ICU, may be calculated based on the patient's respiratory rate, heart rate, diastolic blood pressure, and age. An aggregate score, which is indicative of the likelihood of the patient's imminent need to transfer to the ICU, may be calculated based on the patient's respiratory rate, heart rate, diastolic blood pressure, age, prior ICU stay, oxygen saturation, mental status, the use of in-room oxygen, the BUN measurement, anion gap, platelet count, and white blood cell count. If the calculated aggregate score exceeds a predetermined threshold, the patient may be identified as having a critical risk, and actions may be taken to treat the patient. The risk evaluation may be based further on the patient's mental status, where the patient's mental status may be evaluated based on a game with visual indicators, and may, for example, further be based on or characterized by a quantitative subjective assessment provided by a clinician.

Some embodiments of the present methods for evaluating a (e.g., hospitalized) patient's risk for clinical deterioration, comprise: calculating, using a processor, an aggregate score based on the patient's respiratory rate, heart rate, diastolic blood pressure, and age, the aggregate score being indicative of likelihood of cardiac arrest for the patient; and indicating a level of cardiac arrest risk or clinical deterioration risk for the patient based on an aggregate score that exceeds a predetermined threshold. In some embodiments, the aggregate score is further based on data in an electronic health record corresponding to the patient, the electronic medical record comprising at least one of: a respiratory rate, a blood pressure, a heart rate, an oxygen saturation, a use of supplemental oxygen, a temperature, a white cell count, a hemoglobin, a platelets, a sodium, a potassium, a chloride, a bicarbonate, an anion gap, a blood urea nitrogen, a glucose value, a prior ICU stay, and a BUN measurement. In some embodiments, the patient's respiratory rate, heart rate, diastolic blood pressure and age are the only variables used to evaluate the patient's cardiac arrest risk. In some embodiments, the aggregated score is calculated based on weighting the variables of respiratory rate, heart rate, diastolic blood pressure and age of the patient. Some embodiments further comprise treating the patient identified as having an aggregate score that exceeds a predetermined threshold. In some embodiments, the calculating is based on performing logistic regression on one or more datasets comprising records of a plurality of patients. In some embodiments, the calculating is based on a person-time multinomial logistic regression model (e.g., the calculating may comprise separating time into discrete periods where each patient contributes a record for each period that the patient remained on wards).

Some embodiments of the present methods further comprise: receiving measurements of the patient's respiratory rate, heart rate, diastolic blood pressure, and age; assigning, using the processor, a respiratory rate score based on the respiratory rate, a heart rate score based on the heart rate, a diastolic blood pressure score based on the diastolic blood pressure, and an age score based on the age, each score being indicative of the likelihood of cardiac arrest for the patient; and calculating, using the processor, the aggregate score based on the respiratory rate score, heart rate score, diastolic blood pressure score, and age score. In some embodiments, the aggregate score is calculated based further on the patient's quantitative mental status. Some embodiments further comprise: determining the patient's quantitative mental status based on the patient's answer to at least one multiple-choice question; where the multiple-choice question includes a query regarding at least one of: the current president, the current day, the current month, and the current year. In some embodiments, the patient's respiratory rate, heart rate, diastolic blood pressure, age and quantitative mental status are the only variables used to evaluate the patient's cardiac arrest risk. In some embodiments, the aggregate score is calculated based further on the patient's non-subjective mental status. In some embodiments, the patient's respiratory rate, heart rate, diastolic blood pressure, age and non-subjective mental status are the only variables used to evaluate the patient's cardiac arrest risk. In some embodiments, the aggregate score is calculated based further on the patient's pulse pressure. In some embodiments, the patient's respiratory rate, heart rate, diastolic blood pressure, age and pulse pressure are the only variables used to evaluate the patient's cardiac arrest risk. In some embodiments, the calculating and indicating are automatically performed for two or more times. In some embodiments, the calculating and indicating are automatically performed periodically.

Some embodiments of the present systems for evaluating a (e.g., hospitalized) patient's risk for clinical deterioration, comprise: a processor configured to: calculate an aggregate score based on a patient's respiratory rate, heart rate, diastolic blood pressure, and age, the aggregate score being indicative of the likelihood of cardiac arrest for the patient; and identify a level of cardiac arrest risk or clinical deterioration risk for the patient based on an aggregate score that exceeds a predetermined threshold. In some embodiments, the patient's respiratory rate, heart rate, diastolic blood pressure and age are the only variables used to evaluate the patient's cardiac arrest risk. In some embodiments, the aggregated score is calculated based on weighting the variables of respiratory rate, heart rate, diastolic blood pressure and age of the patient. Some embodiments, further comprise treating the patient identified as having an aggregate score that exceeds a predetermined threshold. In some embodiments, the calculating is based on performing logistic regression on one or more datasets, the one or more datasets comprising cardiac risk records of a plurality of patients. In some embodiments, the calculating is based on a person-time multinomial logistic regression model (e.g., the calculating may comprise separating time into discrete periods where each patient contributes a record for each period that the patient remained on wards).

Some embodiments of the present systems are further configured to: receive measurements of the patient's respiratory rate, heart rate, diastolic blood pressure, and age; assign a respiratory rate score based on the respiratory rate, a heart rate score based on the heart rate, a diastolic blood pressure score based on the diastolic blood pressure, and an age score based on the age, each score being indicative likelihood of cardiac arrest for the patient; and calculate the aggregate score based on the respiratory rate score, heart rate score, diastolic blood pressure score, and age score. In some embodiments, the aggregate score is calculated based further on the patient's quantitative mental status. In some embodiments, the patient's respiratory rate, heart rate, diastolic blood pressure, age and quantitative mental status are the only variables used to evaluate the patient's cardiac arrest risk. In some embodiments, the aggregate score is calculated based further on the patient's non-subjective mental status. In some embodiments, the patient's respiratory rate, heart rate, diastolic blood pressure, age and non-subjective mental status are the only variables used to evaluate the patient's cardiac arrest risk. In some embodiments, the aggregate score is calculated based further on the patient's pulse pressure. In some embodiments, the patient's respiratory rate, heart rate, diastolic blood pressure, age and pulse pressure are the only variables used to evaluate the patient's cardiac arrest risk. In some embodiments, the calculating and indicating are automatically performed for two or more times. In some embodiments, the calculating and indicating are automatically performed periodically.

Some embodiments of the present non-transitory computer-readable media embody a set of instructions executable by one or more processors, the set of instructions configured to perform a method comprising: calculating, using a processor, an aggregate score based on a patient's respiratory rate, heart rate, diastolic blood pressure, and age, the aggregate score being indicative likelihood of cardiac arrest for the patient; and indicating a level of cardiac arrest risk for the patient based on an aggregate score that exceeds a predetermined threshold.

Some embodiments of the present methods and systems are configured for monitoring patients in one or more units of a hospital, an entire hospital, or several hospitals. In some such embodiments are configured to receive (e.g., do receive or include receiving) data pertaining to multiple patients. Such data may be aggregated and scores calculated scores based on the received data. Trends associated with the aggregated data and/or the generated scores may also be calculated, and/or the aggregated and calculated data may be shown in a unified display that facilitates efficient allocation of resources in the hospital unit, the hospital, or the group of hospitals. In some embodiments, the unified display comprises a list. In some embodiments, the list includes aggregate scores and trends associated with the aggregate scores (e.g., a trend or delta generally includes a change in a piece of recorded data or a calculated score over a time period). The list may also include patient names and/or may allow for sorting based on aggregate score and trend. In some embodiments, the list displays objective or subjective recorded health data (e.g., vitals, such as blood pressure, heart rate, AVPU score, etc.). Some embodiments provide the list in a graphical user interface (GUI). In some embodiments, a user of the GUI may view detailed information regarding a recorded data value, an aggregate score, or a trend by selecting (e.g., clicking) the recorded data value, the score, or the trend. In some embodiments, the list is first unsorted or sorted in a default order (e.g., highest-to-lowest score) and a user request specifies a particular sorting of the list. In other embodiments, the list is first unsorted and a configuration setting specifies a particular sorting of the list. In some such embodiments, the configuration setting specifies a stored user request that previously specified a particular sorting of the list.

Some embodiments detect that a patient is suffering from a certain medical condition and display a GUI with more detailed information regarding the medical condition. In some embodiments, this more detailed information entails symptoms and treatment information.

Some embodiments are configured to generate an alarm when a patient's health is deteriorating. In some embodiments, the alarm is generated in response to (1) an aggregate score and a trend of the aggregate score, (2) a recorded data value (e.g., a vital sign) and of the recorded data value, and/or (3) a combination of a recorded data value, aggregate score, and their trends. Such a condition may be automatically detected when the scores, recorded data values (e.g., vital signs), and/or trends meet or exceed a certain threshold. Some embodiments perform the alerting (i.e., generate the alarms) in real time.

In accordance with one or more further embodiments, an early warning system is provided for assisting a plurality of patients manage chronic health conditions. The early system comprises a computer system communicating with client devices operated by the plurality of patients over a communications network. For each patient the computer system is configured to: (a) receive information from the patient or a member of a patient care network on an expected patient activity at a given future time period; (b) determine expected transient local ambient conditions in the patient's surroundings during the expected patient activity at the given future time period; (c) predict health exacerbations for the patient using a stored computer model of the patient based on a desired patient control set-point range, the expected patient activity, and the expected transient local ambient conditions; and (d) proactively transmit a message to the patient or a member of the patient care network before the given future time period, the message alerting the patient or a member of the patient care network of the predicted health exacerbations for the patient and identifying one or more corrective actions for the patient to avoid or mitigate the predicted health exacerbations.

Some embodiments of the present methods for evaluating a user's mental status, comprise: (a) presenting an initial sequence of visual indicators to the user via a display; (b) receiving an input from the user via an input device; (c) comparing the input to the sequence of visual indicators; (d) if the input and the sequence of visual indicators are identical, presenting a subsequent sequence of visual indicators having a length greater than the length of the previous sequence and repeating steps (b)-(e) for the subsequent sequence; and (e) if the input and the sequence of visual indicators are not identical, and if no predetermined criterion has been met, presenting a subsequent sequence of visual indicators having a length less than the length of the previous sequence and repeating steps (b)-(e) for the subsequent sequence; or if a predetermined criterion has been met, assigning a mental status score to the user. In some embodiments, the sequence of visual indicators comprises a plurality of elements having different colors. In some embodiments, the sequence of visual indicators comprises a plurality of elements having different shapes or numbers. In some embodiments, the mental status score is based on a length of the last user input that is identical to a sequence of visual indicators that is presented to the user. In some embodiments, the display and input device are disposed in an portable electronic device. In some embodiments, the portable electronic device is a tablet computer. In some embodiments, the display and input device are unitary. In some embodiments, the display is coupled to a computer. In some embodiments, the predetermined criterion comprises a length of a sequence of visual indicators is equal to one. In some embodiments, the predetermined criterion comprises: a first input of a user is not identical to a sequence of visual indicators having a first length; a second input of a user is identical to a sequence of visual indicators having a second length that is less than the first length; and a third input of a user is not identical to a sequence of visual indicators having a third length that is greater than the second length.

Some embodiments of the present systems for evaluating a user's mental status, comprise: a display configured to present a sequence of visual indicators to a user; an input device configured to receive an input from the user; and a processor configured to: (a) present an initial sequence of visual indicators to a user via the display; (b) receive an input from the user via the input device; (c) compare the input to the sequence of visual indicators; (d) if the input and the sequence of visual indicators are identical, presenting a subsequent sequence of visual indicators having the a length greater than the length of the previous sequence and repeat steps (b)-(e) for the subsequent sequence; and (e) if the input and the sequence of visual indicators are not identical, and if no predetermined criterion has been met, presenting a subsequent sequence of visual indicators having a length less than the length of the previous sequence and repeat steps (b)-(e) for the subsequent sequence; or if a predetermined criterion has been met, assign a mental status score to the user. In some embodiments, the sequence of visual indicators comprises a plurality of elements having different colors. In some embodiments, the sequence of visual indicators comprises a plurality of elements having different shapes or numbers. In some embodiments, the mental status score is based on a length of the last user input that is identical to a sequence of visual indicators that is presented to the user. In some embodiments, the display and input device are disposed in a portable electronic device. In some embodiments, the portable electronic device is a tablet computer. In some embodiments, the display and input device are unitary. In some embodiments, the display is coupled to a computer. In some embodiments, the predetermined criterion comprises a length of a sequence of visual indicators is equal to one. In some embodiments, the predetermined criterion comprises: a first input of a user is not identical to a sequence of visual indicators having a first length; a second input of a user is identical to a sequence of visual indicators have a second length that is less than the first length; and a third input of a user is not identical to a sequence of visual indicators having a third length that is greater than the second length.

Some embodiments of the present electronic (e.g., portable) devices are configured to: (a) present an initial sequence of visual indicators to a user via the display; (b) receive an input from the user via the input device; (c) compare the input to the sequence of visual indicators; (d) if the input and the sequence of visual indicators are identical, presenting a subsequent sequence of visual indicators having a length greater than the length of the previous sequence and repeat steps (b)-(e) for the subsequent sequence; and (e) if the input and the sequence of visual indicators are not identical, and if no predetermined criterion has been met, presenting a subsequent sequence of visual indicators having a length less than the length of the previous sequence and repeat steps (b)-(e) for the subsequent sequence; and if a predetermined criterion has been met, assign a mental status score to the user. In some embodiments, the sequence of visual indicators comprises a plurality of elements having different colors. In some embodiments, the sequence of visual indicators comprises a plurality of elements having different shapes or numbers.

Some embodiments of the present non-transitory computer-readable media embody a set of instructions executable by one or more processors, the set of instructions configured to perform a method comprising: (a) presenting an initial sequence of visual indicators to the user via a display; (b) receiving an input from the user via an input device; (c) comparing the input to the sequence of visual indicators; (d) if the input and the sequence of visual indicators are identical, presenting a subsequent sequence of visual indicators having a length greater than the length of the previous sequence and repeating steps (b)-(e) for the subsequent sequence; and (e) if the input and the sequence of visual indicators are not identical, and if no predetermined criterion has been met, presenting a subsequent sequence of visual indicators having a length less than the length of the previous sequence and repeating steps (b)-(e) for the subsequent sequence; or if a predetermined criterion has been met, assigning a mental status score to the user.

Any embodiment of any of the devices, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments. Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 9 illustrates the Modified Early Warning Score (MEWS).

FIG. 12 illustrates an embodiment of a scale for quantifying a subjective assessment or patient risk, the patient acuity rating (PAR).

FIG. 13 illustrates patient characteristics for PAR.

FIG. 14 illustrates weighted kappa statistics by provider for PAR.

FIG. 15 illustrates PAR sensitivities and specificities.

FIG. 16 illustrates area under the PAR receiver operator characteristics curve by provider.

DETAILED DESCRIPTION OF ILLUSTRATIVE EMBODIMENTS

Figure 1:
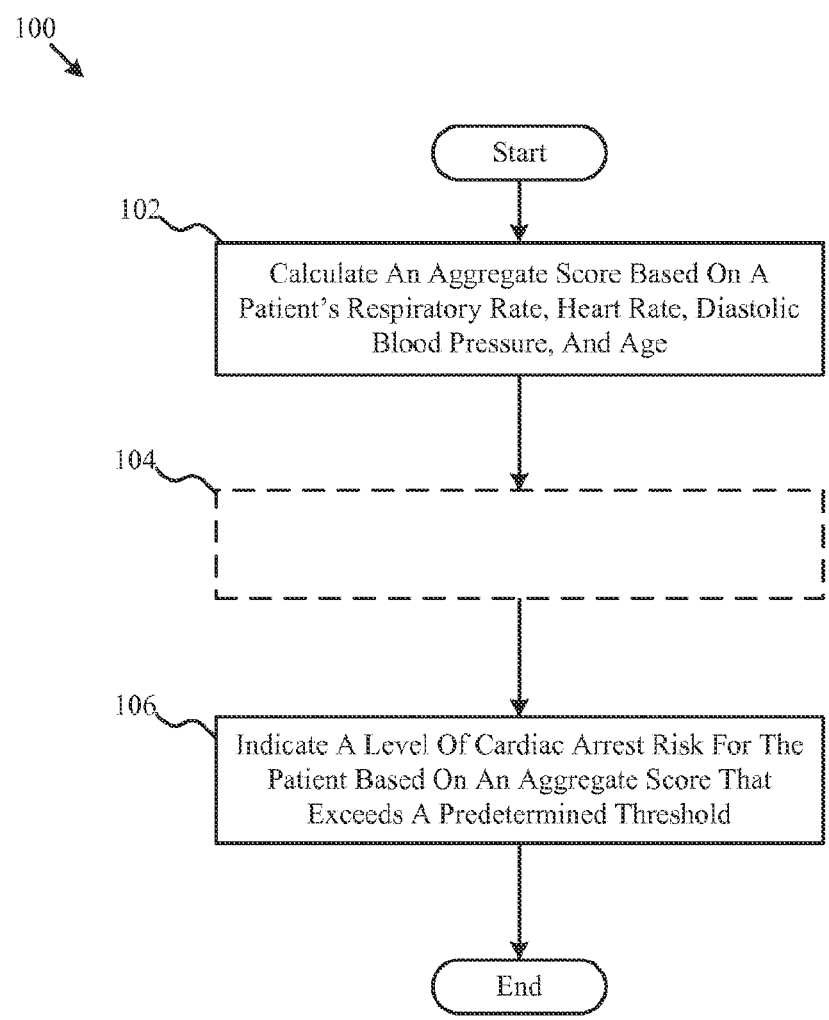
FIG. 1 is a flowchart illustrating one embodiment of the present methods for evaluating a patient's cardiac arrest risk.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a device or system that is configured in a certain way is configured in at least that way, but it can also be configured in other ways than those specifically described.

Various features and advantageous details are explained more fully with reference to the non-limiting embodiments that are illustrated in the accompanying drawings and detailed in the following description. Descriptions of well-known starting materials, processing techniques, components, and equipment may be omitted for brevity. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those having ordinary skill in the art from this disclosure.

The schematic flow chart diagrams that follow are generally set forth as logical flow chart diagrams. As such, the depicted order and labeled steps are indicative of some of the present embodiments. Other steps and methods may be employed that vary in some details from the illustrated embodiments (e.g., that are equivalent in function, logic, and/or effect). Additionally, the format and symbols employed are provided to explain logical steps and should be understood as non-limiting. Although various arrow types and line types may be employed in the flow chart diagrams, they should be understood as non-limiting. Indeed, some arrows or other connectors may be used to indicate only the logical flow of the method. For instance, an arrow may indicate a waiting or monitoring period of unspecified duration between enumerated steps. Additionally, the order in which a particular method occurs may or may not strictly adhere to the order of the corresponding steps shown.

FIG. 1 illustrates one embodiment 100 of the present methods for evaluating a patient's cardiac arrest risk. In some embodiments, the method comprises calculating 102 an aggregate score based on the patient's respiratory rate, heart rate, diastolic blood pressure, and age. The aggregate score is indicative of a likelihood of cardiac arrest for the patient, and thus may be referred to as a cardiac arrest risk score or cardiac arrest risk triage (CART) score. Step 102 may be performed by a processor, such as a CPU of a general-purpose computer, a tablet computer, a mobile device, an embedded device, or the like. Method 100 may comprise one or more optional steps 104, examples of which are described in FIG. 2. Method 100 may further comprise indicating 106 a level of cardiac arrest risk for the patient based on an aggregate score that exceeds a predetermined threshold. For example, the patient may be indicated to have a very high cardiac arrest risk, high cardiac arrest risk, intermediate cardiac arrest risk, or low cardiac arrest risk. In some embodiments, a predetermined threshold may be determined based on historical data of patients who had cardiac arrests. For example, aggregated scores may be calculated for a period of time for a plurality of patients who had cardiac arrest risk based on step 102, resulting in a sequence of aggregate scores for each of the plurality of patients calculated at different times. Sequences of aggregate scores for patients who actually had cardiac arrest may be identified and compared. Based on changes of a patient's aggregated score and occurrence of cardiac arrest, a correlation between the patient's cardiac arrest risk and aggregate score may be derived, and one or more thresholds may be determined based on the correlation, and/or based on the resources of a hospital in which the thresholds are to be implemented (e.g., as described in more detail below).

In some embodiments, the aggregated score is calculated based on weighting the variables of respiratory rate, heart rate, diastolic blood pressure, demographics (e.g., age), and/or laboratory data (e.g., potassium, anion gap, platelet count). The weighting value for each variable may be, for example, calculated from historical data of patients that have experienced cardiac arrest while admitted to a hospital. For example, one or more datasets for a plurality of patients having cardiac arrest risk may be obtained, where the datasets comprise measurements of the respiratory rate, heart rate, diastolic blood pressure, demographics (e.g., age), and/or laboratory data (e.g., potassium, anion gap, platelet count), and where a sequence of measurements measured in a certain period may correspond to each patient. A logistic regression may be performed on the one or more datasets to determine a correlation of each of the variables to a patient's cardiac arrest risk, and weighting values can be determined based on the correlation, where the stronger a variable's correlation to cardiac arrest risk is, the larger the weighting values assigned to a variable is. This model may be updated and/or recalculated on an ongoing (e.g., periodic, intermittent, or continuous) basis as new and/or more-detailed information is added to the model).

In some embodiments, a patient's cardiac arrest risk score is based only on the patient's (e.g., weighted indicators of the patient's) respiratory rate, heart rate, diastolic blood pressure, and age (as may be the evaluation of the patient's cardiac arrest risk, such as based on the cardiac arrest risk score). In some embodiments, a patient's cardiac arrest risk score is based only on the patient's (e.g., weighted indicators of the patient's) respiratory rate, heart rate, diastolic blood pressure, age, and a quantitative and/or non-objective indicator of mental status. In some embodiments, method 100 is automatically performed repeatedly (e.g., intermittently, periodically, or continuously) over a period of time, for example, for the whole period of the patient's stay in a hospital or in a portion of a hospital (e.g., general in-patient ward). Method 100 may also be automatically performed periodically, for example, every 15 minutes, every hour, or the like.

Figure 2:
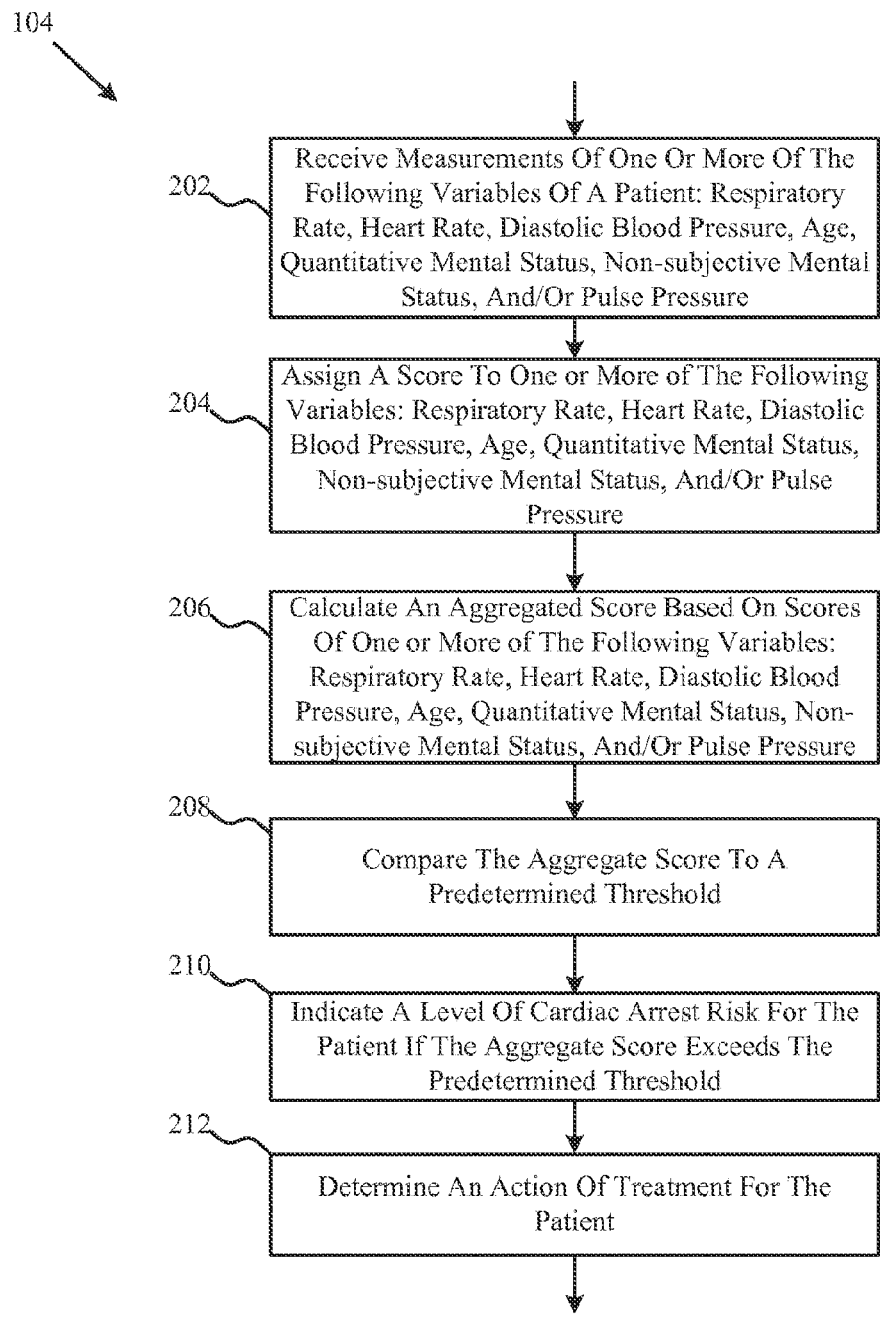
FIG. 2 is a flowchart illustrating one embodiment of the present methods for evaluating a patient's cardiac arrest risk.

FIG. 2 illustrates one embodiment of additional/optional steps 104 for method 100 in FIG. 1. In some embodiments, a measurements of one or more of: a patient's respiratory rate, heart rate, diastolic blood pressure, demographics (e.g., age), and/or laboratory data (e.g., potassium, anion gap, platelet count) quantitative mental status, non-subjective mental status (with respect to a healthcare provider), and/or pulse pressure can be received in a step 202. At least some of the data may be obtained from an electronic health record (EHR). In a step 204, a score may be assigned to one or more of: respiratory rate, heart rate, diastolic blood pressure, age, quantitative mental status, non-subjective mental status, and/or pulse pressure, where the score assignment to a variable is based on the received measurement of that variable. In some embodiments, the patient's mental status may be evaluated by the method described in FIG. 3A.

In step 206, an aggregated score can be calculated based on scores of one or more of the following variables: respiratory rate, heart rate, diastolic blood pressure, demographics (e.g., age), and/or laboratory data (e.g., potassium, anion gap, platelet count), quantitative mental status, non-subjective mental status, and pulse pressure. The calculated aggregated score can then be compared to one or more predetermined thresholds in step 208. If the aggregated score exceeds one or more predetermined thresholds, step 210 indicates a level of the patient's risk of clinical deterioration or cardiac risk. In some embodiments, a range of cardiac arrest risk scores are divided into two or more levels (e.g., three levels, four levels), such as, for example, based on available resources of an hospital. Levels of risk may, for example, correspond to: very high cardiac arrest risk, high cardiac arrest risk, intermediate cardiac arrest risk, or low cardiac arrest risk, as described above.

In step 212, an action of treatments is determined for the patient. For example, if the patient is determined to have very high cardiac arrest risk, an automatic rapid response team (RRT) call may be performed to request a RRT to attend and/or treat the patient; if the patient is determined to have a high cardiac arrest risk, one or more health care providers (e.g., a nurse and/or a physician) may be called to perform a critical care consult on the patient; if the patient is determined to have an intermediate cardiac arrest risk, increased monitoring may be performed on the patient; and/or if the patient is determined to have a low cardiac arrest risk, the current healthcare management may be continued for the patient.

In some embodiments, the action of treatment for the patient and/or the predetermined threshold to trigger the action may depend on the available resources of a healthcare provider, agreements between the patient and the healthcare provider, and/or other factors. For example, if a healthcare provider has only resources to treat 5% of its patients having cardiac arrest risk with RRT, the health care provider may customize the threshold for aggregated score to trigger RRT, such that only the 5% of the patients with the highest scores receives RRT treatment. For example, in a hospital with an average ward population of 100 patients and enough resources (e.g., Rapid Response Teams) to attend to 5 patients at any given time, the threshold for the highest level of risk (e.g., triggering a visit by an RRT) may be correlated to the historical risk scores of the 5% of patients with the highest risk scores. In another example, if a healthcare does not have enough resources, the healthcare provider may decide that current healthcare management is continued for patients determined to have both low and intermediate cardiac arrest risk.

In some embodiments, an aggregate score is calculated based only on variables of a patient's respiratory rate, heart rate, diastolic blood pressure and age. In another embodiment, an aggregate score is calculated based only on variables of a patient's respiratory rate, heart rate, diastolic blood pressure, age and quantitative mental status. In yet another embodiment, an aggregate score is calculated based only on variables of a patient's respiratory rate, heart rate, diastolic blood pressure, age and non-subjective mental status. In yet another embodiment, an aggregate score is calculated based only on variables of a patient's respiratory rate, heart rate, diastolic blood pressure, age and pulse pressure.

Figure 3A:
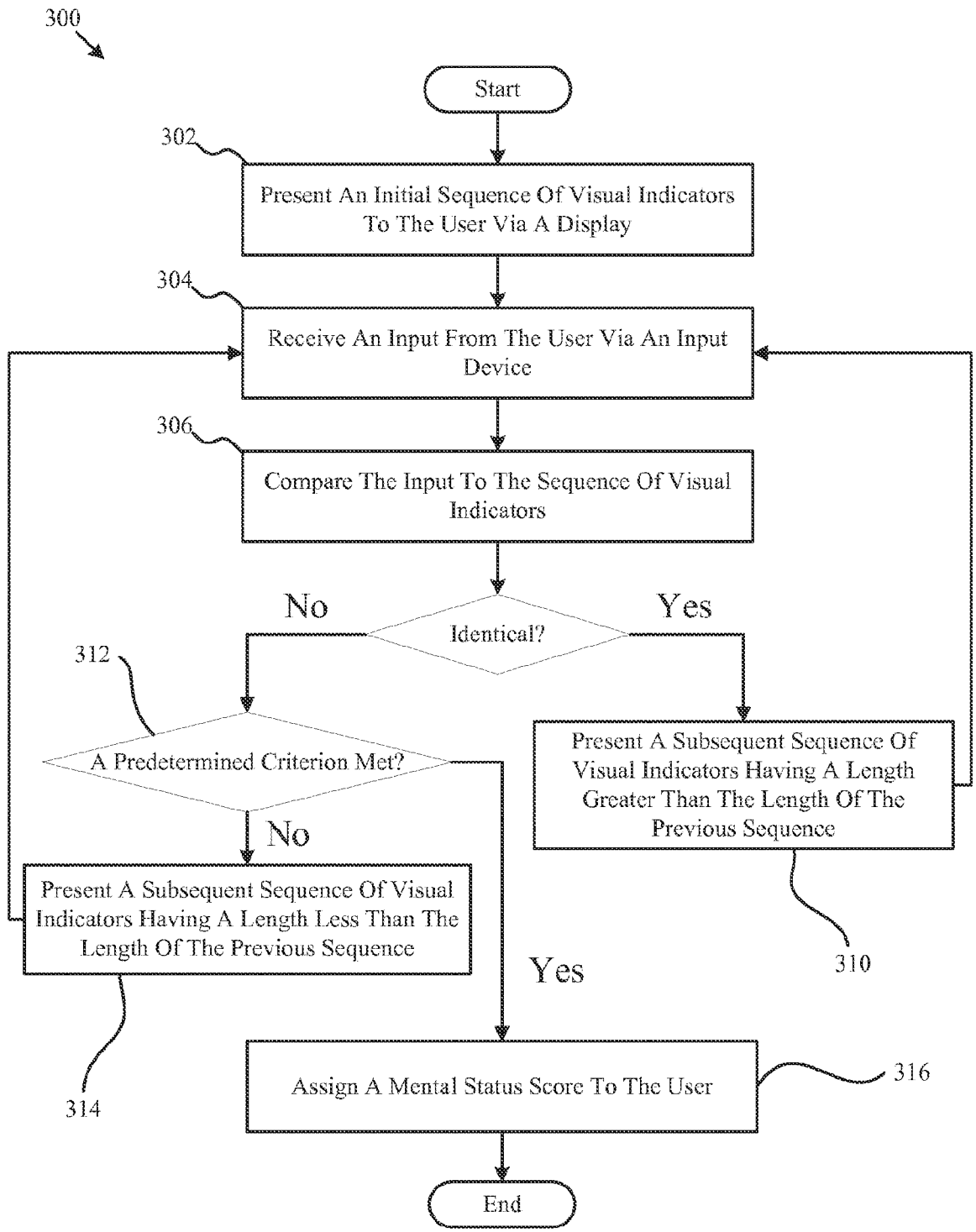
FIG. 3A is a flowchart illustrating one embodiment of the present methods for evaluating a patient's mental status.

FIG. 3A illustrates one embodiment of a method 300 for evaluating a user's mental status. The user's mental status may be used in method 100 described in FIG. 1 to evaluate the user's cardiac arrest risk. In some embodiments, method 300 comprises: presenting 302 an initial sequence of visual indicators to the user via a display. In step 304, an input from the user is received via an input device (which may be unitary with the display, such as, for example a touch-screen of a tablet computer). The input from the user is compared in step 306 to the sequence of visual indicators presented to the user. If the input sequence from the user is identical to the sequence of visual indicators presented to him/her, step 310 presents a subsequent sequence of visual indicators having a length greater than the length of the previous sequence, and the appropriate ones of steps 304-316 can be repeated for the subsequent sequence.

If the input sequence from the user is not identical to the sequence of visual indicators presented to him/her, step 312 determines whether a predetermined criterion has been met. If no predetermined criterion has been met, step 314 presents a subsequent sequence of visual indicators having the a length less than the length of the previous sequence, and the appropriate ones of steps 304-316 can be repeated for the subsequent sequence. At step 312, if a predetermined criterion has been met, a mental status score is assigned to the user in step 316.

In some embodiments, the sequence of visual indicators presented to the user comprises a plurality of elements having different colors, and/or different shapes. For example, in some embodiments, a blue square, a red square, a green square, and a yellow square can be flashed in a sequence (e.g., blue, red, green, and yellow). In such embodiments, an input from the user can be prompted by flashing the shapes in the sequence (e.g., blue, red, green, and yellow), and then displaying all four of the shapes such that the user can indicate the sequence by touching the shapes on a screen in the order in which they were flashed or otherwise displayed to the users. In other embodiments, an input from the user can be proved by flashing numbered blue and gold (or any other color(s) of) boxes (e.g., two blue boxes numbered '1' and '2' and two gold boxes numbered '1' and '2') can be flashed in a sequence (e.g., blue, red, green, and yellow). In other embodiments, the indicators displayed to the user may have the same color and different shapes (e.g., circle, triangle, square, oval), and/or may have any other characteristics (e.g., patterns) that permit the user to distinguish between the indicators in the sequence. The mental status score assigned to the user may be based on the length of the last user input that is identical to a sequence of visual indicators that is presented to the user.

In some embodiments, a predetermined criterion may comprise the length of a sequence of visual indicators presented to the user is equal to a minimum number (e.g., 1, 2, 3, or more). A predetermined criterion may also comprise a plurality of items. For example, in one embodiment, the predetermined criterion is not met until: a first input of the user is not identical to a sequence of visual indicators having a first length; a second input of a user is identical to a sequence of visual indicators have a second length that is less than the first length; and a third input of a user is not identical to a sequence of visual indicators having a third length that is greater than the second length (e.g., having a third length that is equal to the first length). For example, in some embodiments, an initial sequence includes three visual indicators; if the patient correctly matches the initial sequence, then the length of the next sequence is increased by two to five visual indicators; but if the patient fails to correctly match the sequence, then the length of the sequence is decreased by one to two visual indicators; and so on, until the patient fails to match two sequences of visual indicators, at which point the patient's performance is scored according to the longest sequence the patient was able to correctly match.

In some embodiments, the sequence may begin with three lit rectangles. If the user repeats the sequence correctly, the sequence may increases by two lit rectangles, to a total of five lit rectangles. Each time the user repeats a sequence correctly, the sequence length may be increased by two lit rectangles (e.g., 5+2=7, 7+2=9, and so on). If the user fails to correctly repeat the sequence, the sequence length may decrease by one (e.g., 9−1=8, 8−1=7, and so on). After the user fails to repeat sequences twice, the user is asked to repeat the sequence for a last time. If the user repeats the sequence correctly, she may obtain a score equivalent to the current sequence length (e.g., score of 7 for a sequence length of 7 lit rectangles). If she fails to repeat the sequence correctly, she may obtain a score equivalent to the longest sequence last repeated correctly, which may be equal to one less than the current sequence length (e.g., score of 6 for a sequence length of 6 lit rectangles). Although a sequence increase of two, and a sequence decrease of one, are described, other increments in sequence increase or decrease may be used.

In some embodiments, the display and input device used in method 300 can be disposed in a portable electronic device. The portable electronic device may be a tablet computer, such as an iPad, or a smart phone, or the like. The input device may be a physical keyboard, or a virtual keyboard displayed on a display device, where a user can input information by touching the virtual keyboard. Alternatively, the input device may be a regular keyboard or mouse coupled to a computer. The display device may be a monitor coupled to a computer.

One or more series of questions may be presented to the user before beginning the sequence of visual indicators at block 302. For example, multiple-choice questions may be presented to the user to determine a mental state of the user. The multiple-choice questions may include questions about the current year, the current month, the current day, the current day of the week, the current president, and/or other current events. The correctness of the answers may be considered as factors when determining the aggregate score for the user.

Figure 3B:
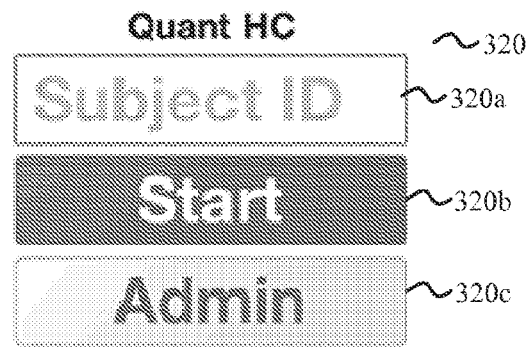
FIGS. 3B-3O are screen shots illustrating one embodiment of the present methods of a mental status scoring application for a smartphone.
Figure 3C:
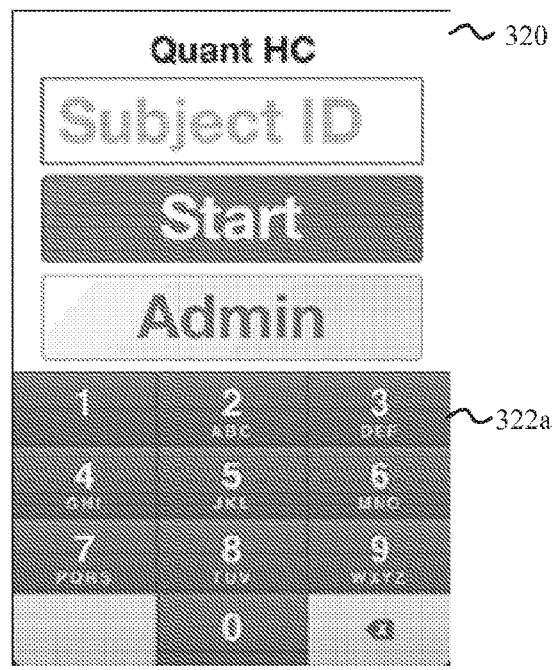
Figure 3D:
Figure 3E:
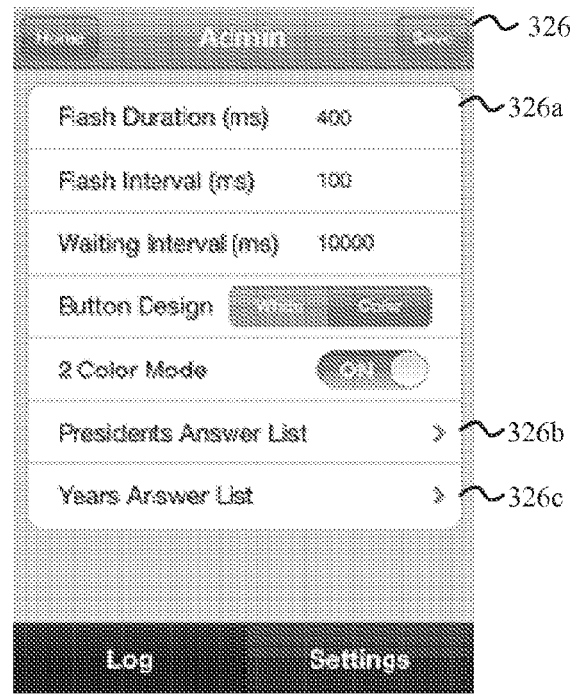
Figure 3F:
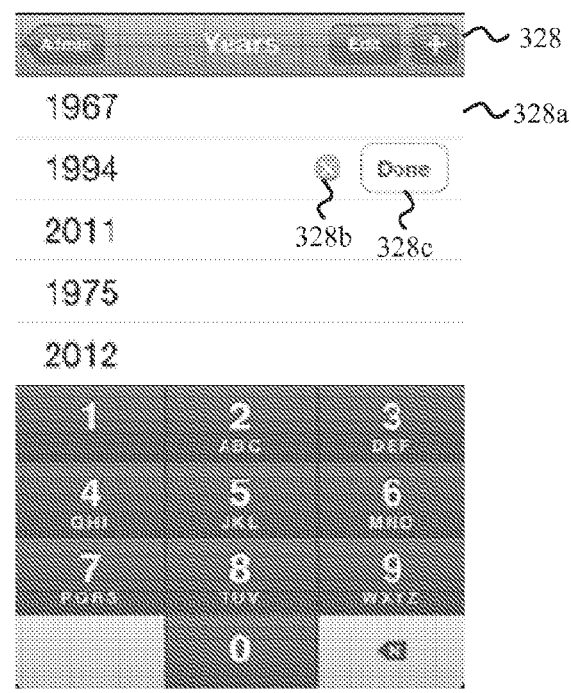
Figure 3G:
Figure 3H:
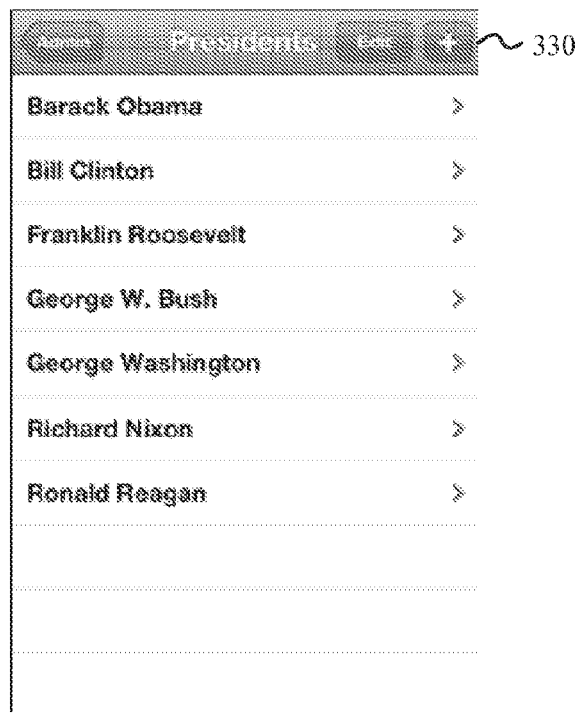
Figure 3I:
Figure 3L:
Figure 3M:
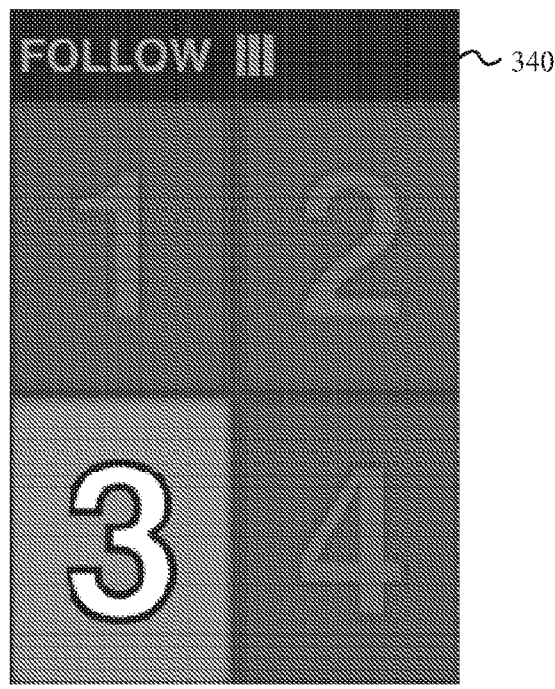
Figure 3N:
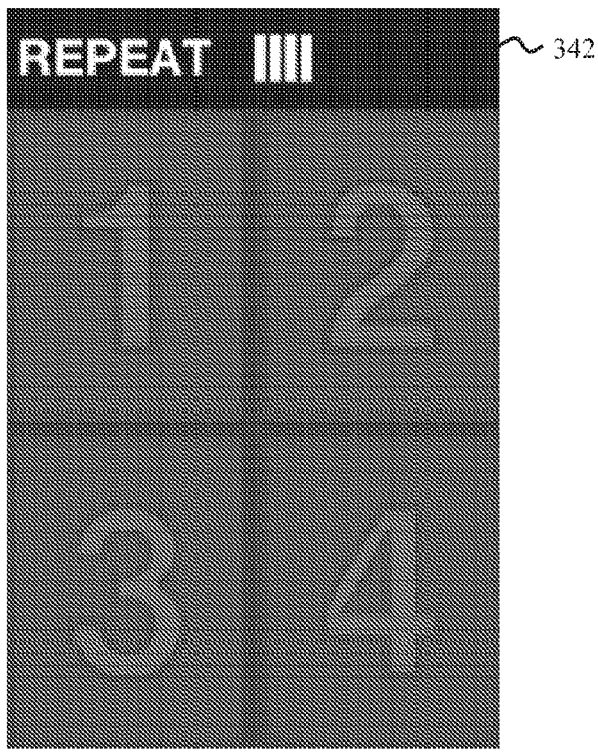
Figure 3O:
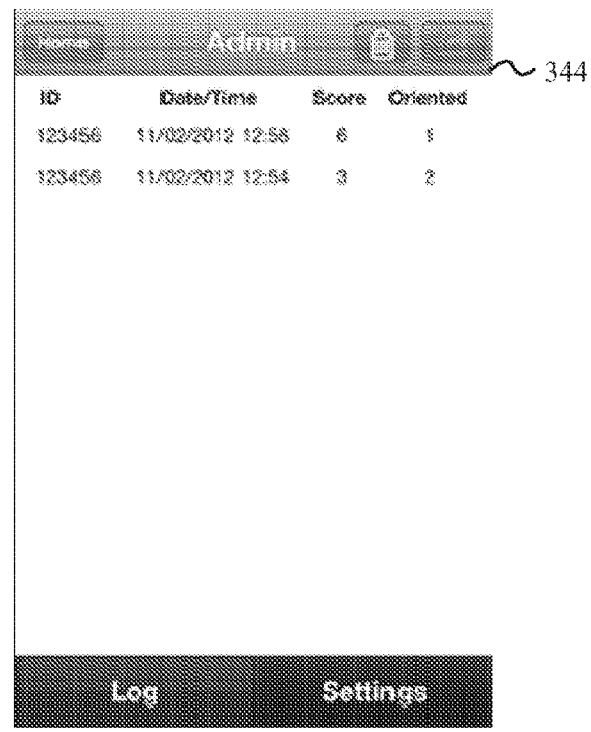

FIGS. 3B-3O depict screen shots of an implementation of a mental status scoring application, described above with reference to FIG. 3A, for a smartphone according to some embodiments of the disclosure. FIG. 3B illustrates an initial log-on screen 320 presented to a user. Screen 320 may include an entry box 320a for a subject ID, which indicates to the application the patient completing the test. The subject ID may match a patient ID, social security number, driver license number, name, nickname, or other value for identifying a patient. Screen 320 may also include a button 320b to start the test for the entered subject ID and a button 320c to edit administration information for the application. A user may enter a subject ID into entry box 320a through a keyboard. If no keyboard is available, such as on a touch-screen-based smart phone, a virtual keyboard 322a may be presented to the user on screen 320 as illustrated in FIG. 3C. The user may enter their identification number, such as "123456," with the virtual keyboard as illustrated in screen 324 of FIG. 3D. The patient ID may be cleared by selecting a delete button 324a.

If admin button 320c of FIG. 3B is activated, the user may be taken to an administration screen 326 illustrated in FIG. 3E. When the user requests access to administrative information, the user may first be prompted with a screen requesting a password or other authorization information to determine if the user is authorized to access administrative information. If authorization is verified, then the user may have an opportunity to adjust settings 326a on screen 326, including a flash duration, flash interval, waiting interval, button design, and/or color mode. Administrative screen 326 may also include access to the multiple-choice question lists. For example, when one of the multiple-choice questions may be to select the current president, a presidents answer list 326b may appear on the administrative screen 326. In another example, when one of the multiple-choice questions may be to select the current year, a year answer list 326c may appear on the administrative screen 326.

If the user selects to edit year answer list 326c, edit screen 328 of FIG. 3F may be presented to the user. Screen 328 includes a listing 328a of the possible year answers. When a user selects one of the answers for editing, the user may be presented with a delete button 328b and a done button 328c. The user may delete the answer by selecting the delete button 328b, upon which the user may enter a new year for the answer in entry 328d of FIG. 3G. Similarly, if the user selects to edit president answer list 326b, edit screen 330 of FIG. 3H may be presented to the user.

If the user is not an administrator, the user enters his subject ID in entry box 320a of FIG. 3A and selects start button 320b. The user may then be taken to screen 332 of FIG. 3I, which queries the user about the current year. A number of answers from year answer list 328a of FIG. 3F may be presented in the screen 332. The user may select one of the years, such as by tapping the region on the screen corresponding to the current year. Likewise, similar screens, such as screen 334 of FIG. 3J, screen 336 of FIG. 3K, and screen 338 of FIG. 3L may be presented to the user to query the user's mental status.

After the multiple-choice questions have been presented, the user may be taken to one or more screens that illustrate an initial sequence of visual indicators as described with reference to blocks 302-314 of FIG. 3A. One example of a screen with visual indicators is illustrated in screen 340 of FIG. 3M. Screen 340 includes four differently-labeled boxes, which may be different colors. A pattern is illustrated to the user on screen 340, which the user must follow. Then, a similar screen 324 of FIG. 3N will be displayed to allow the user to repeat the pattern by touching an area of the screen corresponding to the pattern previously displayed.

After a score is calculated for a patient, the score may be stored in the memory of the device. The stored scores may be recorded along with the patient ID and a date/time the test was completed. A table from the device memory may be displayed on a screen 344 of FIG. 3O to an administrator. Although only a portion of data is presented in screen 344, the device may store a much larger amount of information regarding completed tests. For example, the device may store the subject ID, a device ID, a round number (e.g., a number of attempts made by the subject), a start time, an end time, a sequence length, the sequence shown during the round (e.g., 341421214), the sequence entered by the subject during the round (e.g., 341212124), a score assigned to the subject for the round (e.g., an integer between 0 and 10), a status of the round (e.g., failed, passed, or aborted), a session start time for the subject including all the rounds, a session end time for the subject including all the rounds, a score for the session (e.g., an integer between 0 and 10), a color mode for the round, a button type for the round, the year selected by the subject, the year choices presented to the subject, the month selected by the subject, the month choices presented to the subject, the day selected by the subject, the day choices presented to the subject, the president selected by the subject, and/or the president choices presented to the subject.

In the following description, numerous specific details are provided, such as examples of programming, software modules, user selections, network transactions, database queries, database structures, hardware modules, hardware circuits, hardware chips, etc., to provide a thorough understanding of disclosed embodiments. One of ordinary skill in the art will recognize, however, that embodiments of the invention may be practiced without one or more of the specific details, or with other methods, components, materials, and so forth. In other instances, well-known structures, materials, or operations are not shown or described in detail to avoid obscuring aspects of the invention.

Figure 4:
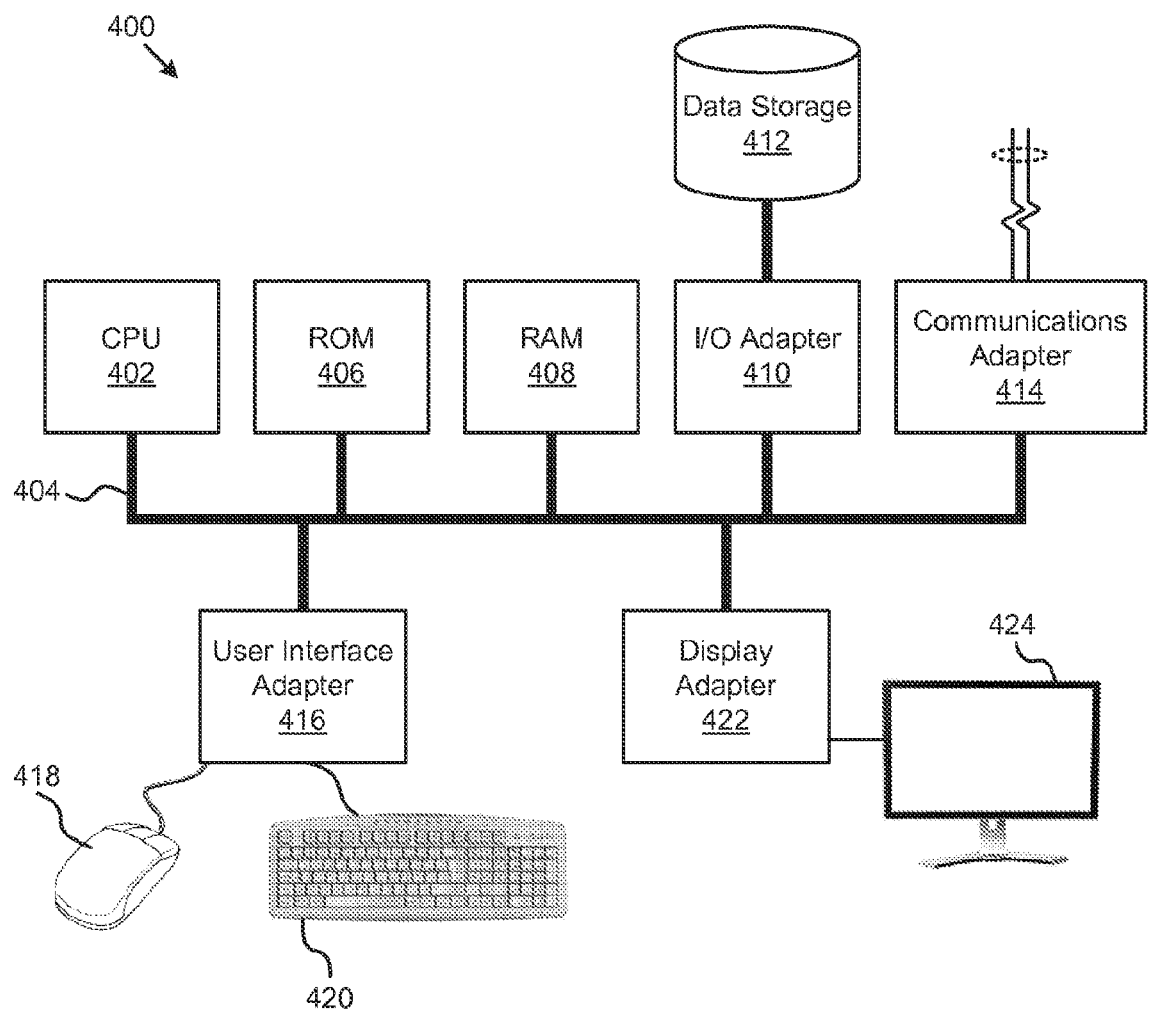
FIG. 4 is a block diagram illustrating one embodiment of the present systems for evaluating a patient's mental acuity and/or mental status.

FIG. 4 illustrates one embodiment of the present systems 400 for evaluating a patient's cardiac arrest risk and/or mental status. In some embodiments, the central processing unit (CPU) 402 is coupled to the system bus 404. CPU 402 may be a general purpose CPU or microprocessor. The present embodiments are not restricted by the architecture of CPU 402, any type of CPU 402 may be used that is able to function as described in this disclosure. CPU 402 may execute various logical instructions according to disclosed embodiments. For example, CPU 402 may execute machine-level instructions according to the exemplary operations described in FIGS. 1-3, where the instructions may be stored at data storage 412, RAM 408, ROM 406, or received the from communications adapter 414, or input from user input interface adapter 416, or other means.

The system 400 may include Random Access Memory (RAM) 408, which may be SRAM, DRAM, SDRAM, or the like. System 400 may utilize RAM 408 to store the various data structures used by a software application configured to evaluate a user's cardiac arrest risk, and/or mental status. System 400 may also include Read Only Memory (ROM) 406 which may be PROM, EPROM, EEPROM, optical storage, or the like. The ROM may store configuration information for booting system 400. RAM 408 and ROM 406 hold user and system data.

System 400 may also include an input/output (I/O) adapter 410, a communications adapter 414, a user interface adapter 416, and a display adapter 422. I/O adapter 410 and/or user interface adapter 416 may, in certain embodiments, enable a user to interact with the system 400 in order to input information, for example, a sequence of visual indicators for evaluating a user's mental status, as described in FIG. 3. In a further embodiment, display adapter 422 may display a graphical user interface associated with a software or web-based application for evaluating a user's cardiac arrest risk and/or mental status.

For example, display adapter 422 may be controlled by CPU 402 to display an aggregate score indicating likelihood of the user's cardiac arrest risk, and/or an action to be taken based on the user's aggregate score via display device 424. Display adapter 422 may be controlled by CPU 402 to display a sequence of visual indicators to a user via display device 424 to evaluate the user's mental score, and/or to display the user's mental status score via display device 424 based on the evaluation.

I/O adapter 410 may connect to one or more storage devices 412, such as one or more of a hard drive, a Compact Disk (CD) drive, a floppy disk drive, a tape drive, to the system 400. Storage devices 412 may store electronic health records (EHR). Storage devices 412 may also store results from previously completed mental status tests. Communications adapter 414 may be adapted to couple system 400 to other devices, and/or a network, which may be one or more of a wireless link, a LAN and/or WAN, and/or the Internet. Other devices in communication with system 400 through the communications adapter 414 may communicate electronic health records to system 400. User interface adapter 416 couples user input devices, such as a keyboard 420 and a pointing device 418, to system 400. Display adapter 422 may be driven by CPU 402 to control what is displayed by display device 424.

Communications adapter 414 may receive measurements related to a patient, such as the patient's respiratory rate, heart rate, diastolic blood pressure, age, quantitative mental status, non-subjective mental status (with respect to a healthcare provider), pulse pressure, or other information of the patient, where these measurements may be stored at data storage 412. Communications adapter 414 may receive one or more datasets which comprise historical data of a plurality of patients having cardiac arrest risk, where the one or more datasets may be stored at data storage 412. For each patient, there may be a sequence of measurements, of variables such as those listed above, measured during a period of time.

The one or more datasets which comprise historical data of a plurality of patients having cardiac arrest risk may be analyzed by executing a plurality of instructions via CPU 402. For example, logistic regression may be performed on the one or more datasets to find a correlation between each of the variables (such as a patient's respiratory rate, heart rate, diastolic blood pressure, age, quantitative mental status, non-subjective mental status, pulse pressure, or the like) and the patient's cardiac arrest risk. Based on the correlation, CPU 402 may calculate a weighing value for each variable based on the variable's strength of correlation to a patient's cardiac arrest risk. CPU 402 may further calculate an aggregate score indicating a patient's cardiac arrest risk based on the weighting value for each variable, and the measured value for each variable.

In some embodiments, system 400 may act as a stand-alone device for evaluating a patient's cardiac arrest risk and/or mental status. For example, system 400 may be operated by a patient and/or a health care provider (such as a nurse, a physician, or the like) in a hospital ward, at the patient's home, or other places, to evaluate the patient's cardiac arrest risk and/or mental status.

In some embodiments, system 400 may act as a server. For example, data storage 412 may store one or more sets of instructions configured to perform methods described in FIGS. 1-3. The one or more sets of instructions may be in the form of software, or software applications downloadable from a user device, such as a general-purpose computer, a tablet computer, a smart phone, other types of portable electronic devices, such as those described in FIG. 5. A user may download the instructions from system 400 through a network connected to system 400, e.g. by communications adapter 414. The network may be wired or wireless network, such as a LAN, a WAN, a MAN, and/or the Internet.

Figure 5:
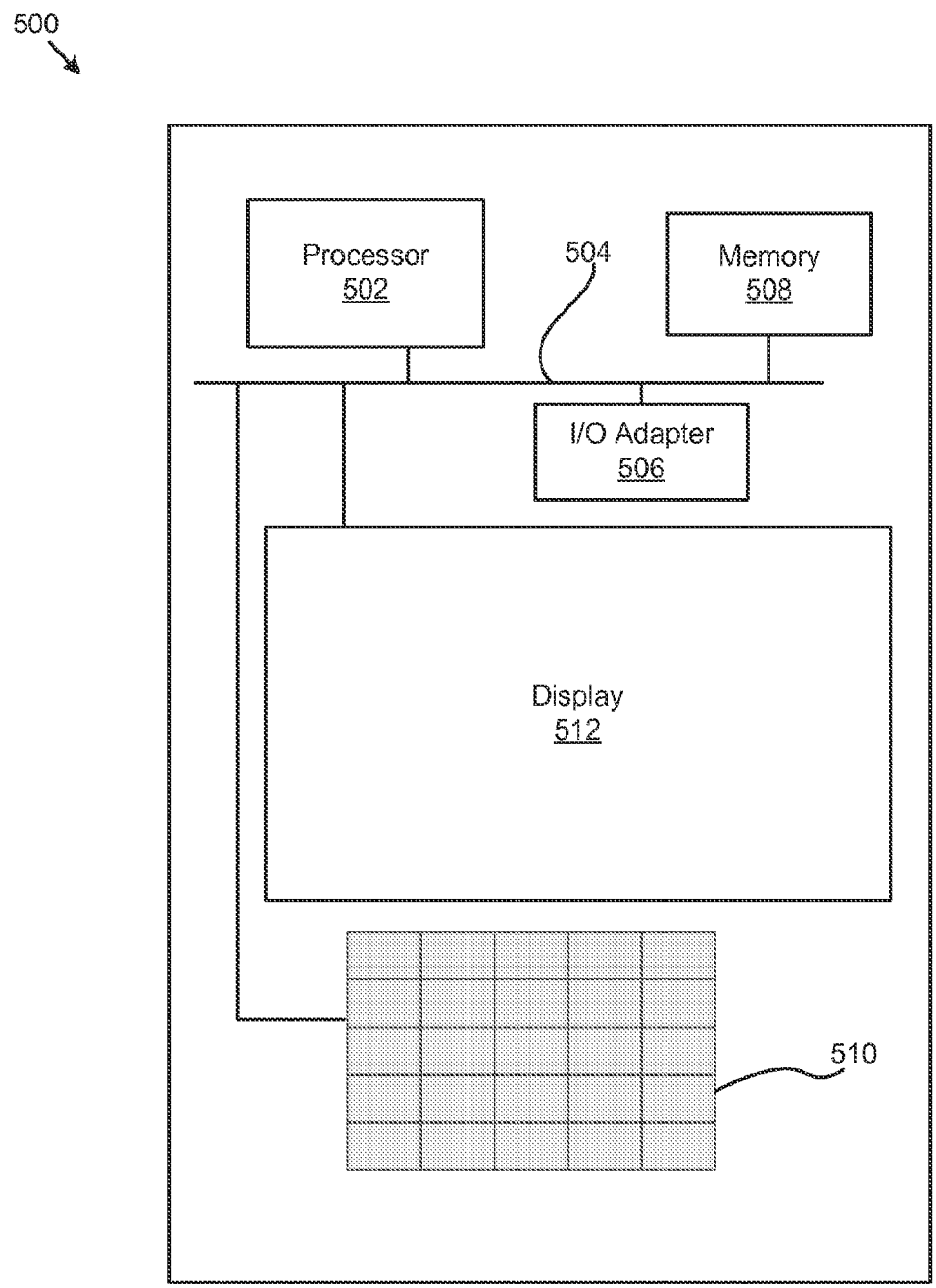
FIG. 5 is a block diagram illustrating one embodiment of the present apparatuses for evaluating a patient's mental acuity and/or mental status.

For example, a patient or a healthcare provider can download a software application for cardiac arrest risk evaluation and/or mental status evaluation from system via a user device (e.g. an iPhone, an iPad, a general purpose computer, or a portable electronic device such as those described in FIG. 5) through network connection. Cardiac arrest risk evaluation and/or mental status evaluation may be performed on a user device, and/or results may be sent back to a separate system 400 via a network connection. Upon receiving results of cardiac arrest risk evaluation and/or mental status evaluation from a user device, system 400 can display the received results via display device 424, and/or trigger certain action of treatment for the patient, for example, automatically calling a nurse, a physician, a RRT, or other healthcare providers.

In some embodiments, system 400, acting as a server, may initiate evaluations of a patient's cardiac arrest risk and/or mental status evaluation, either in an automatic fashion or a controlled fashion. For example, a nurse, a physician, or other healthcare providers may control system 400 to send a request for evaluating a patient's cardiac arrest risk and/or mental status to a user device, and receive evaluation results from the user device.

Disclosed embodiments are not limited to the architecture of system 400. Rather, system 400 is provided as an example of one type of computing device that may be adapted to perform instructions, such as those exemplified in FIGS. 1-3. For example, any suitable processor-based device may be utilized including without limitation, including laptop computers, tablet computers (such as iPads), smart phones, personal data assistants (PDAs), computer game consoles, and multi-processor servers. Moreover, the present embodiments may be implemented on application specific integrated circuits (ASIC) or very large scale integrated (VLSI) circuits. In fact, persons of ordinary skill in the art may utilize any number of suitable structures capable of executing logical operations according to the disclosed embodiments.

FIG. 5 illustrates one embodiment of a portable electronic device 500 for evaluating a patient's cardiac arrest risk and/or mental status. In some embodiments, portable electronic device 500 may comprise a processor 502, I/O adapter 506, memory 508, input device 510, and a display 512, where each component may be connected to a bus 504.

Portable electronic device 500 may be a tablet computer (such as a iPad), a smart phone (such as an iPhone or an Android-based platform), a gaming device, an iPod, or the like. Portable electronic device 500 may be configured to perform one or more set of instructions, such as those illustrated in FIGS. 1-3.

Processor 502 may be a microprocessor or the like. The present embodiments are not restricted by the architecture of processor 502, so long as processor 502 supports the modules and operations as described herein. Processor 502 may execute various logical instructions according to disclosed embodiments. For example, processor 502 may execute machine-level instructions according to the exemplary operations described in FIGS. 1-3. The instructions may be stored at memory 508, or received from I/O adapter 506, or input by a user via input device 510, or other means.

Memory 508 may comprise RAM, which may be SRAM, DRAM, SDRAM, ROM, ROM, which may be which may be PROM, EPROM, EEPROM, optical storage, or other kinds of non-transitory storing devices. Portable electronic device 500 may utilize memory 508 to store the various data structures used by a software application configured to evaluate a user's cardiac arrest risk, and/or mental status. For example, memory 508 may store one or more set of instructions capable of executing the methods described in FIGS. 1-3. Memory 508 may also store measurements of one or more patients, such as the patients' respiratory rate, heart rate, diastolic blood pressure, age, quantitative/non-subjective mental status, pulse pressure, or other clinical and/or demographical information of the patients, where such measurements may be received via I/O adapter 506. Memory 508 may also store one or more datasets that comprise historical data of a plurality of patients having cardiac arrest risk, where the one or more datasets may be received via I/O adapter 506. For each patient in the datasets, there may be a sequence of measurements, of variables such as those listed above, measured during a period of time.

The one or more datasets which comprise historical data of a plurality of patients having cardiac arrest risk may be analyzed by executing a plurality of instructions via the processor. For example, logistic regression may be performed on the one or more datasets to find a correlation between each of one or more variables (such as a patient's respiratory rate, heart rate, diastolic blood pressure, age, quantitative mental status, non-subjective mental status, pulse pressure, or the like) and the patient's cardiac arrest risk. Based on the correlation, the processor 502 may calculate a weighing value for each variable based on the variable's strength of correlation to a patient's cardiac arrest risk. Processor 502 may further calculate an aggregate score indicating a patient's cardiac arrest risk based on the weighting value for each variable, and the measured value for each variable.

I/O adapter 506, input device 510, and/or display 512 may, in certain embodiments, enable a user to interact with portable electronic device 500 in order to input information, for example, a sequence of visual indicators for evaluating a user's mental status, as described in FIG. 3. In a further embodiment, display 512 may display a graphical user interface associated with a software or web-based application for evaluating a user's cardiac arrest risk and/or mental status.

For example, display 512 may be controlled by processor 502 to display an aggregate score indicating likelihood of the user's cardiac arrest risk, and/or an action to be taken based on the user's aggregate score. Display 512 may be further controlled by processor 512 to display a sequence of visual indicators to a user via display 512 to evaluate the user's mental score, and/or to display the user's mental status score based on the evaluation, for example, according to the method described in FIG. 3.

Input device 510 may be a physical keyboard. Alternatively, input device 510 may be a virtual keyboard embedded in the display. For example, display 512 may be configured to display a virtual keyboard when applicable, where a user can touch the virtual keyboard on the display to input information.

In some embodiments, portable electronic device 500 may act as a stand-alone device for evaluating a patient's cardiac arrest risk and/or mental status. For example, portable electronic device 500 may be operated by a patient, and/or a health care provider (such as a nurse, a physician, or the like) in a hospital ward, at the patient's home, or other places, to evaluate the patient's cardiac arrest risk and/or mental status.

In some embodiments, portable electronic device 500 may be connected to a server, such as those described in FIG. 4, through a network. The network may be wired or wireless network, such as a LAN, a WAN, a MAN, and/or the Internet. Portable electronic device 500 may be configured to download a software application configured to perform methods, such as those described in FIGS. 1-3, to evaluate a patient's cardiac arrest risk and/or mental status. For example, a user may download the a software application from system 400, through a network, portable electronic device 500, and evaluate his/her cardiac arrest risk and/or mental status using the downloaded software application via portable electronic device 500. Evaluation results may be sent, via portable electronic device 500, to a server, such as system 400. Actions of treatments for the user may be taken by a healthcare provider, such as a nurse, a physician, a RRT, or the like, based on evaluation results received from the patient.

EXAMPLES

The following describe scenarios that may be used with various embodiments of the disclosed invention. These examples are not intended to be limiting, but rather to provide specific uses for different embodiments of the disclosed invention.

Cardiac Arrest Risk Evaluation

Models for predicting a patient's cardiac risk were statistically derived. The prediction model derives a cardiac arrest risk triage (CART) score to predict cardiac arrest (CA) of a patient, and actions to treat the patient may be taken based on the CART score, for example, triggering a rapid response team (RRT). The CART score model was compared to the Modified Early Warning Score (MEWS), a known RRT activation criterion. The CART score model was validated by comparing its ability to identify patients transferred to the intensive care unit (ICU) to the MEWS.

1. Patient Data

The study was conducted at an academic, tertiary care hospital with approximately 500 inpatient beds. Demographic data for all patients were obtained from administrative databases. Time and location stamped vital signs, including temperature, blood pressure, heart rate, oxygen saturation, respiratory rate, and mental status were obtained from the hospital's electronic medical record (EPIC, Verona, Wis.). Pulse pressure index (pulse pressure divided by systolic blood pressure) was also calculated. Mental status was collapsed from four drop-down menu fields in the electronic medical record (orientation, level of consciousness, motor response, and responsiveness) into one score (alert, responsive to voice, responsive to pain, and unresponsive (AVPU)).

A total of 47427 patients that were hospitalized from November 2008 to January 2011 and had documented ward vital signs were included in the study. These patients were divided into three cohorts: patients who suffered a CA on the wards, patients who had a ward to intensive care unit (ICU) transfer, and patients who had neither of these outcomes (controls). The total of 47427 patients in the study included 88 CA patients, 2820 ICU transfers, and 44519 controls.

Patients who suffered a CA, defined as the loss of a palpable pulse with attempted resuscitation, on the ward were identified using a prospectively collected and verified CA quality improvement database. If a patient had more than one CA, only data prior to the first arrest were used. Those who had both a ward CA and a ward to ICU transfer were only counted as CA patients. ICU transfer patients were identified using the hospital's admission, transfer, and discharge administrative database. If a patient had more than one ward to ICU transfer, only data before the first event were included.

Only ward vital signs from admission until discharge (controls), first ICU transfer (ICU patients) or first ward CA were included in the study. If a CA patient also had a previous ICU transfer, only vital signs following the patient's last ICU transfer until CA were included. Vital signs within 30 minutes of CA were excluded because the goal was to predict the event with enough time to potentially intervene.

Patient demographic data are shown in Table 1. Compared to controls, CA patients were older (mean age 64±16 vs. 54±18; P<0.001), had a longer length of stay (median 11 (IQR 5-26) vs. 3 (IQR 1-5) days; P<0.001), and had a lower survival to discharge rate (31% vs. 99.7%; P<0.001). CA patients were more likely to have a prior ICU stay (41% vs. 9%; P<0.001) and RRT call during the study period (7% vs. 0.3%; P<0.001) than control patients. Compared to controls, ICU transfer patients were older (mean age 60±16 vs. 54±18; P<0.001), had a longer length of stay (median 11 (IQR 7-19) vs. 3 (IQR 1-5) days; P<0.001), and lower survival to discharge rate (85% vs. 99.7%; P<0.001).

TABLE 1

Patient Characteristics

| Characteristic | Cardiac arrest patients (n = 88) | ICU transfer patients (n = 2820) | Controls (n = 44519) |
|---|---|---|---|
| Age, mean (SD), years | 64 (16)* | 60 (16)* | 54 (18) |
| Female sex | 50 (57) | 1364 (48)* | 25444 (57) |
| Admitting service | | | |
| Medical | 65 (73)* | 1560 (55)* | 27804 (62) |
| Surgical | 23 (26)* | 1223 (43)* | 13962 (31) |
| Unknown | 0 (0)* | 37 (1)* | 2753 (6) |
| Length of stay, median (IQR) | 11 (5-26)* | 11 (7-19)* | 3 (1-5) |
| Hours of ward data, median (IQR) | 51 (22-166) | 40 (13-103)* | 51 (26-108) |
| Prior ICU stay | 36 (41)* | 423 (15)* | 3998 (9) |
| RRT call during study period | 6 (7)* | 274 (10)* | 116 (0.3) |

TABLE 1-continued

Patient Characteristics

| Characteristic | Cardiac arrest patients (n = 88) | ICU transfer patients (n = 2820) | Controls (n = 44519) |
|---|---|---|---|
| Survived to discharge | 27 (31)* | 2410 (85)* | 44399 (99.7) |

Abbreviations:
IQR, interquartile range;
RRT, rapid response team;
ICU, intensive care unit.
*Denotes statistically different than controls at P < 0.05
Data are shown as number (percentage) unless otherwise specified.

2. Model Derivation a. Multivariate Logistic Regression

Each patient's maximum and minimum value of each vital sign documented on the ward from admission until discharge (controls) or CA was used for model derivation because patients have varying numbers of vital signs collected on the ward and may have abnormalities at different time points before CA. All vital signs and patient age were investigated as potential predictors of CA. Vital sign and age cut-off thresholds were chosen using inflection points from locally weighted least squares regression (LOWESS) smoother curves and refined using univariate logistic regression by combining categories with similar odds ratios.

Stepwise multivariate logistic regression with backwards elimination was performed to derive the final model using the Akaike information criterion (AIC). This measure of model fit penalizes models with large numbers of variables, which is consistent with the goal of developing a simple, parsimonious model. To create the CART score, the beta coefficients from the final multivariate model were multiplied by a factor (this factor equals to 9 in this example, as shown in Table 3) to create a scoring system with cut-off scores with the same sensitivity and specificity as the MEWS at the threshold often cited in the literature (>4) to allow direct comparison between the scoring systems.

Stepwise regression resulted in a final model, which contained five variables: respiratory rate, heart rate, diastolic blood pressure, pulse pressure index, and age. The final model is presented in Table 2.

TABLE 2

Model derivation results for candidate models in stepwise logistic regression

| Model variables* | Variable removed | P-value for variable removal | AIC |
|---|---|---|---|
| RR, HR, DBP, Age, PPI, O2Sat, SBP, Temp, MS | Full model | — | 1145 |
| RR, HR, DBP, Age, PPI, O2Sat, SBP, Max Temp, MS | Min Temp | 0.96 | 1143 |
| RR, HR, DBP, Age, PPI, O2Sat, Max SBP, Max Temp, MS | Min SBP | 0.72 | 1139 |
| RR, HR, DBP, Age, Min PPI, O2Sat, Max SBP, Max Temp, MS | Max PPI | 0.66 | 1135 |
| RR, HR, DBP, Age, Min PPI, O2Sat, Max SBP, Max Temp | Mental status | 0.36 | 1134 |
| RR, HR, DBP, Age, Min PPI, O2Sat, Max SBP | Max Temp | 0.37 | 1133 |
| RR, HR, DBP, Age, Min PPI, O2Sat | Max SBP | 0.29 | 1132 |

TABLE 2-continued

Model derivation results for candidate models
in stepwise logistic regression

| Model variables* | Variable removed | P-value for variable removal | AIC |
|---|---|---|---|
| RR, HR, DBP, Age, Min PPI | O2Sat | 0.26 | 1131 |
| RR, HR, Min DBP, Age, Min PPI | Max DBP | 0.10 | 1131 |

Abbreviations:
AIC, Akaike information criteria;
AUC, area under the receiver operating characteristic curve;
RR, respiratory rate;
HR, heart rate;
DBP, diastolic blood pressure;
PPI, pulse pressure index;
O2sat, oxygen saturation;
SBP, systolic blood pressure;
Temp, temperature;
MS, mental status;
Max, maximum;
Min, minimum
*Variables are both maximum and minimum vital signs unless otherwise noted except oxygen saturation (minimum only), heart rate (maximum only), and respiratory rate (maximum only).

Minimum respiratory rate and minimum heart rate were not investigated in the multivariable model because they were not significant predictors of CA in univariate analysis. Pulse pressure index was dropped from the final model for simplicity because it must be calculated and is less intuitive than traditional vital signs, and its removal did not change the area under the receiver operating characteristic curve (AUC) of the model (0.84 for both models). The predictor cut-offs, beta coefficients, and the CART score are shown in Table 3.

TABLE 3

Derived cardiac arrest prediction model

| Vital Sign | Cardiac arrests, n (%)$^a$ [n = 88] | Controls, n (%)$^a$ [n = 44519] | Beta coefficient | Score |
|---|---|---|---|---|
| Respiratory rate | | | | |
| <21 | 21 (24) | 29997 (67) | Reference | 0 |
| 21-23 | 19 (22) | 8118 (18) | 0.9 | 8 |
| 24-25 | 17 (19) | 3688 (8) | 1.4 | 12 |
| 26-29 | 12 (14) | 1732 (4) | 1.7 | 15 |
| >29 | 19 (22) | 984 (2) | 2.4 | 22 |
| Heart rate | | | | |
| <110 | 41 (47) | 33710 (76) | Reference | 0 |
| 110-139 | 32 (36) | 9911 (22) | 0.5 | 4 |
| >139 | 15 (17) | 898 (2) | 1.4 | 13 |
| Diastolic BP | | | | |
| >49 | 42 (48) | 33783 (76) | Reference | 0 |
| 40-49 | 28 (32) | 8869 (20) | 0.5 | 4 |
| 35-39 | 6 (7) | 1007 (2) | 0.6 | 6 |
| <35 | 12 (14) | 860 (2) | 1.5 | 13 |
| Age | | | | |
| <55 | 22 (25) | 21025 (47) | Reference | 0 |
| 55-69 | 27 (31) | 13962 (31) | 0.5 | 4 |
| >69 | 39 (44) | 9532 (21) | 1.0 | 9 |

$^a$Results reported are number (percent) of cardiac arrest and control patients with maximum (respiratory rate and heart rate) and minimum (diastolic blood pressure) vital sign values in each category.
Abbreviations:
BP, blood pressure After model derivation, every simultaneous vital sign set for CA and control patients was scored using the MEWS and the CART score. If any variable was missing for score calculation, the most recent value was imputed, similar to what would be done in clinical practice. If a patient had no previous values of the missing variable then a normal value was imputed. Each patient's highest MEWS and CART score was used to create receiver operating characteristic (ROC) curves for detecting CA. The area under the ROC curve (AUC) for each model was calculated by the trapezoidal rule, and the ROC curves were compared using the method of DeLong. This analysis was repeated during model validation by scoring every vital sign set for ICU transfer and control patients and then comparing the ROC curves for the MEWS and CART score.

b. Person-Time Logistic Regression Model

Alternatively or additionally, a person-time multinomial regression model may be used to predict cardiac arrest, while accounting for ICU transfers. In a person-time model, a survival analysis technique for evaluating data may be employed. This technique may involve separating time into discrete periods where each patient contributes a record for each period that the patient remained on the wards. The person-time model may be designed to take into account competing risks, time-varying covariates, and non-proportional hazards. The model may use the same number of observations for each patient per time period. Thus, the model may reduce or remove the bias that may occur when sicker patients have more frequent vital sign observations.

In some embodiments, data may be separated into eight-hour time periods, and a sensitivity analysis may be performed using four-hour intervals. The vital signs and laboratory values measured closest to the beginning of each time period may be used for that period, and a normal (median) value may be imputed if the patient did not have any previous values of a particular variable. Potential predictor variables included in the study may be age, whether or not the patient had a previous ICU admission, vital signs, and/or laboratory values. Time may be entered into the model as a linear term for parsimony, and a sensitivity analysis may be performed by entering higher degree polynomial terms to determine if they altered the predictor variable coefficients significantly. All continuous predictor variables may be modeled linearly, and a p-value of <0.05 may be used for variable selection to decrease the chance of overfitting the model. The linear combination of the regression coefficients may be linearly transformed to create a positive score by adding twenty and then multiplying by four for ease of presentation. Changes in the score over time may be graphed using lowess smoother curves for the 48 hours before cardiac arrest, ICU transfer, and/or in a random 48 hours for controls.

3. Continuous Monitoring and Clinical Decisions

The mean CART scores for CA patients, controls, and ICU transfer patients were compared every eight hours in the 48-hour time period prior to the event, using vital sign sets measured closest to but before each eight-hour time point. A randomly selected 48-hour period was used for each control patient for score calculation.

Figure 6:
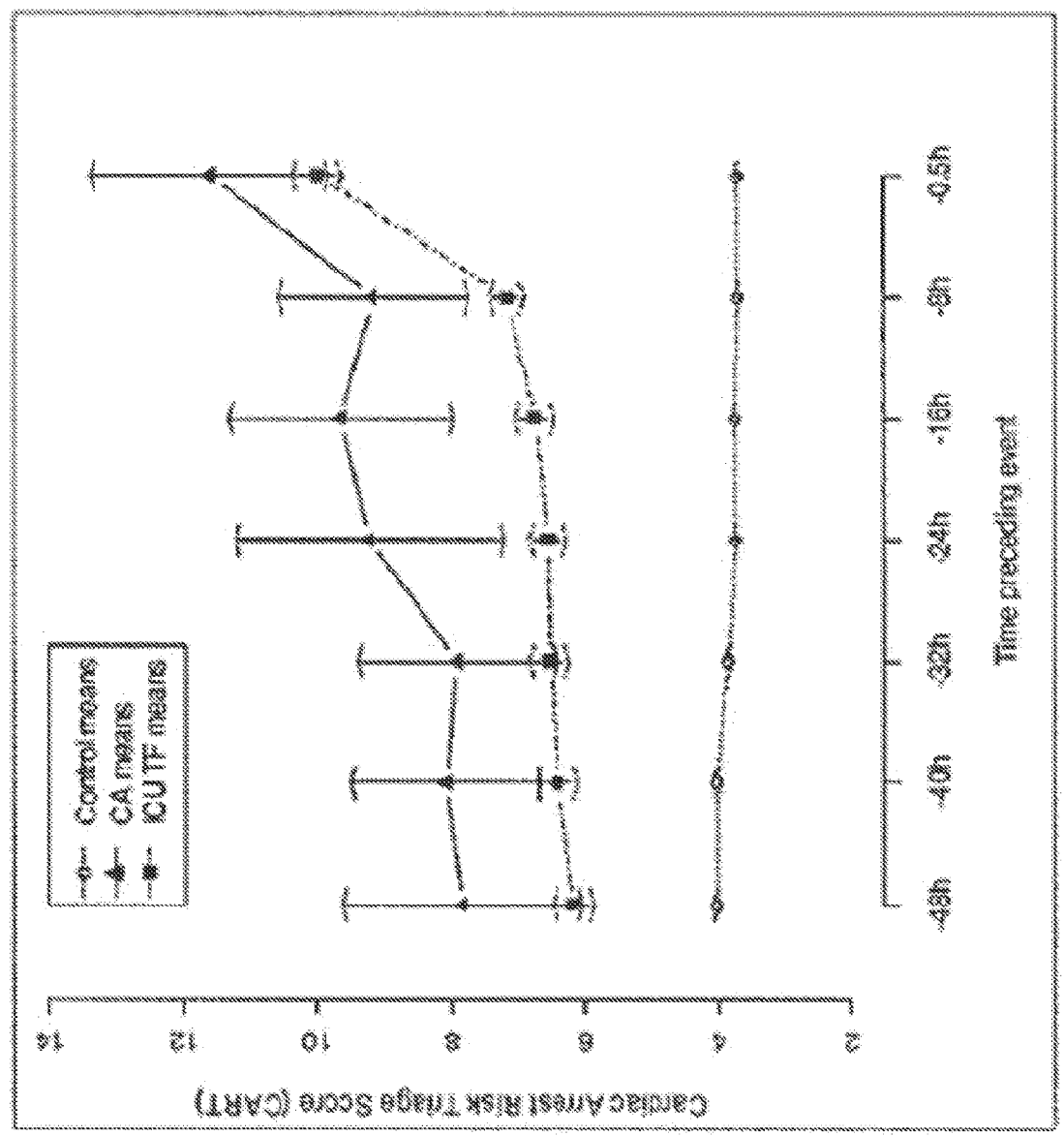
FIG. 6 illustrates change in CART over time prior to cardiac arrest, ICU transfer, and discharge.

The change in mean CART over time for CA, ICU transfer, and control patients is shown in FIG. 6. The mean CART scores were statistically different between CA patients and controls (8±6 vs. 4±4; P<0.001) and between ICU transfer patients and controls (6±6 vs. 4±4; P<0.001) at 48 hours prior to the event, and the differences increased leading up to the event. Mean CART scores were significantly higher for CA patients compared to ICU transfers at 48 hours and 24 hours but not at 30 minutes before the event (9±8 vs. 10±10; P=0.08).

Figure 7:
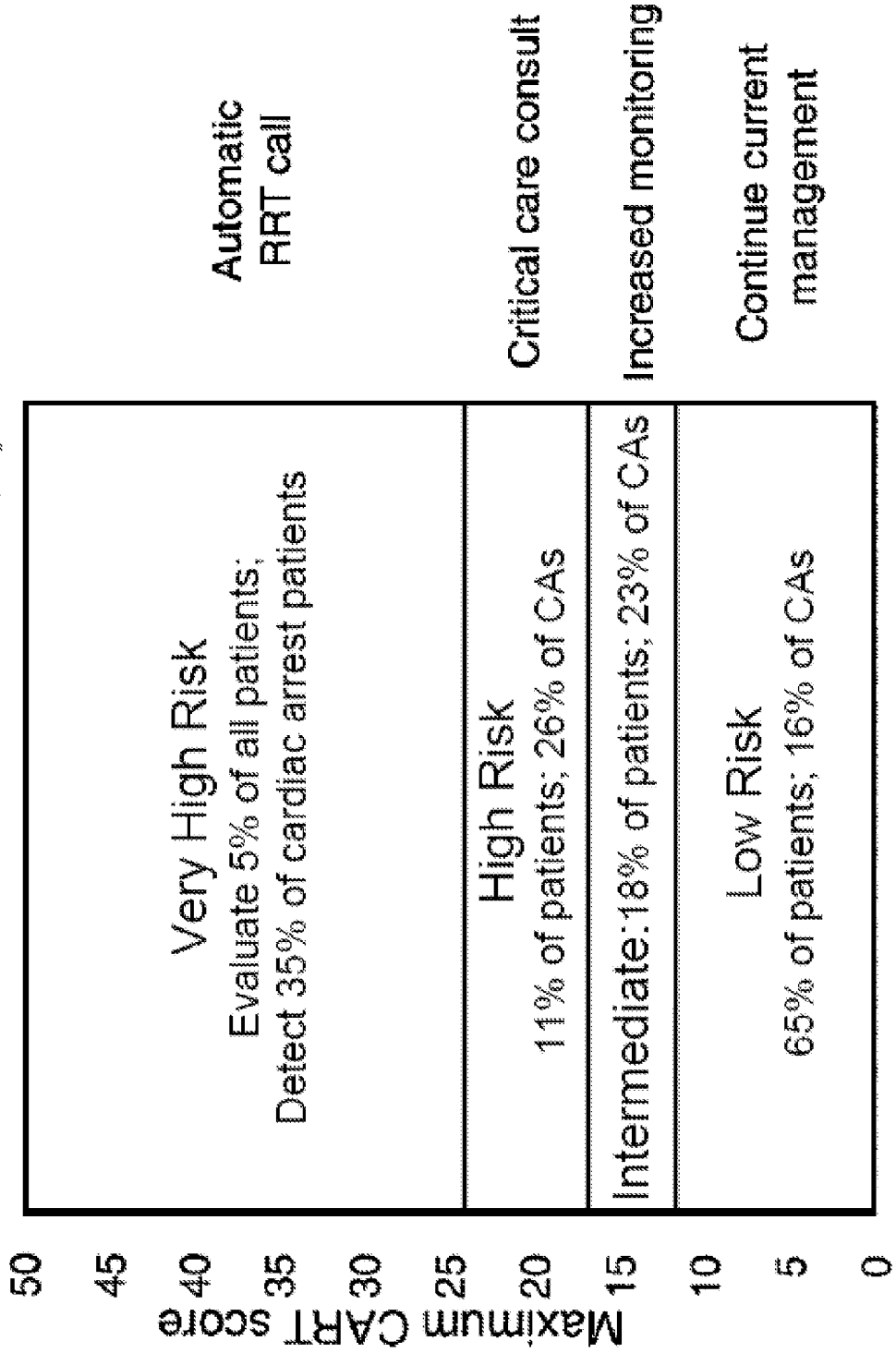
FIG. 7 illustrates one embodiment of a correlation between CART score and possible clinical responses.

FIG. 7 illustrates possible CART score scale of a patient and possible clinical decisions for the patient based on the CART score. Thresholds for CART scores may be determined for indicating the likelihood of cardiac arrest risk for a patient. For example, if a patient's CART score is higher than 25, the patient may be determined to have a very high cardiac arrest risk, and an automatic RRT call may be triggered to provide the patient special treatment; if a patient's CART score is between 15 and 25, the patient may be determined to have a high cardiac arrest risk, and critical care consult may be provided to the patient; if a patient's CART score between 10 and 15, the patient may be determined to have an intermediate cardiac arrest risk, and increased monitoring may be provided the patient; and if a patient's CART score is lower than 10, the patient may be determined to have a low cardiac arrest risk, and current healthcare management may be continued for the patient. The cut-off threshold of CART score of a patient to trigger a certain treatment may be determined based on available resources of a healthcare provider.

Figure 8:
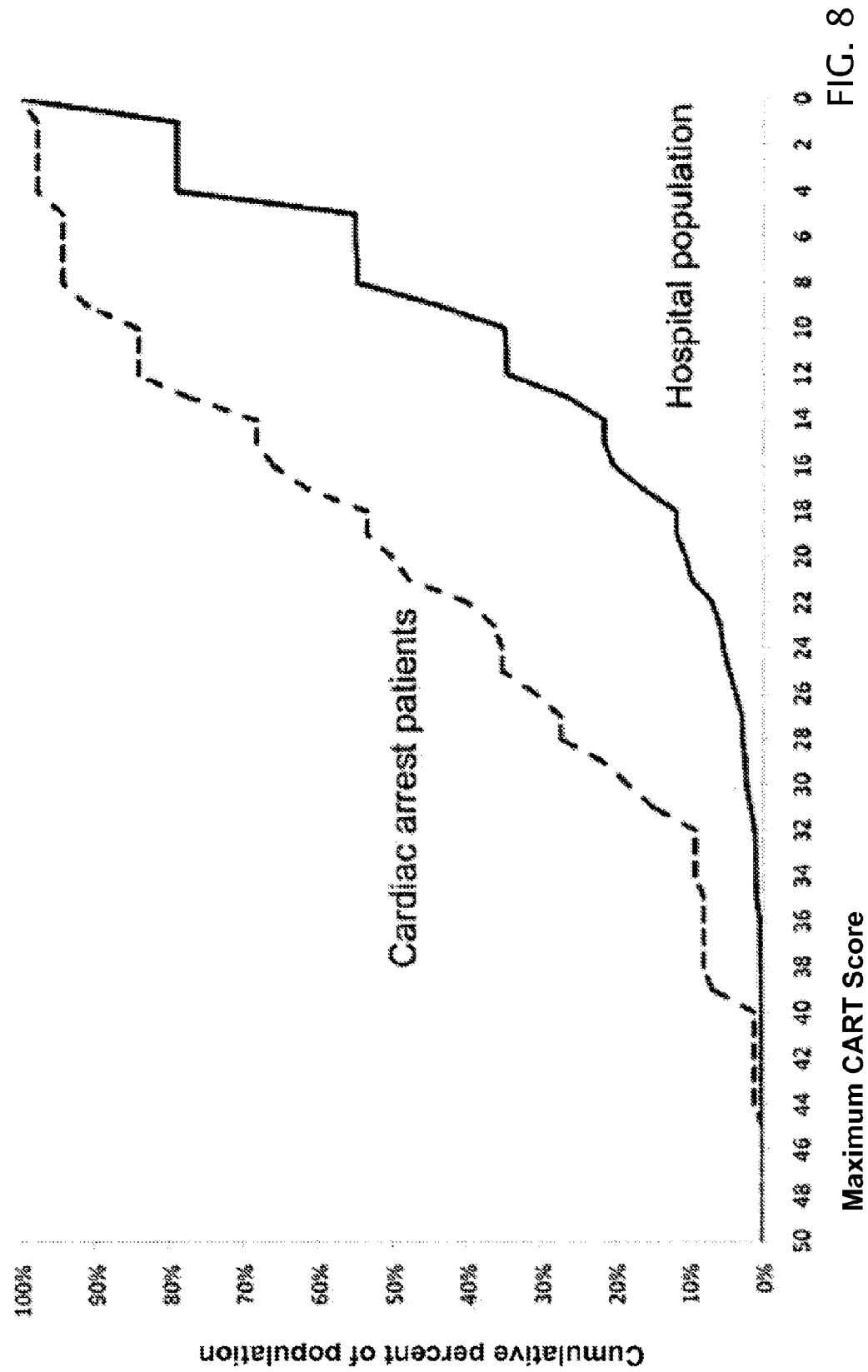
FIG. 8 illustrates cumulative percentage of cardiac arrest patients and percentage of the total hospital ward population.

FIG. 8 illustrates the cumulative percent of both CA patients and the entire hospital population on the wards as the CART score cut-off threshold decreases. The cut-off threshold of CART score of a patient to trigger a certain treatment may be determined from this figure. For example, drawing a vertical line up from a specific CART score denotes the percent of the ward population with a score of that value or higher and the percent of CA patients that were identified at that cut-off threshold. Similarly, drawing a horizontal line from a specific cumulative percent of population denotes the CART score of that value or higher and the CA patients that were identified at the cut-off threshold. For example, drawing a horizontal line from the value 10% on the cumulative percentage population axis, the horizontal line would intercept with the CA curve (dotted line) at a point that approximately corresponds to a CART score value of 38. Therefore, if the hospital only have resources to provide only 10% of its patient with RRT treatment, it can determine the cut-off threshold of CART score for triggers RRT is 38.

4. Comparison to MEWS

Beta coefficients of the final CART score model were multiplied by a factor of nine to create the CART score, as shown in Table 3, because this resulted in a model containing cut-points with the same sensitivity and specificity as the MEWS at cut-off >4. The MEWS score system is shown in FIG. 9.

Figure 10:
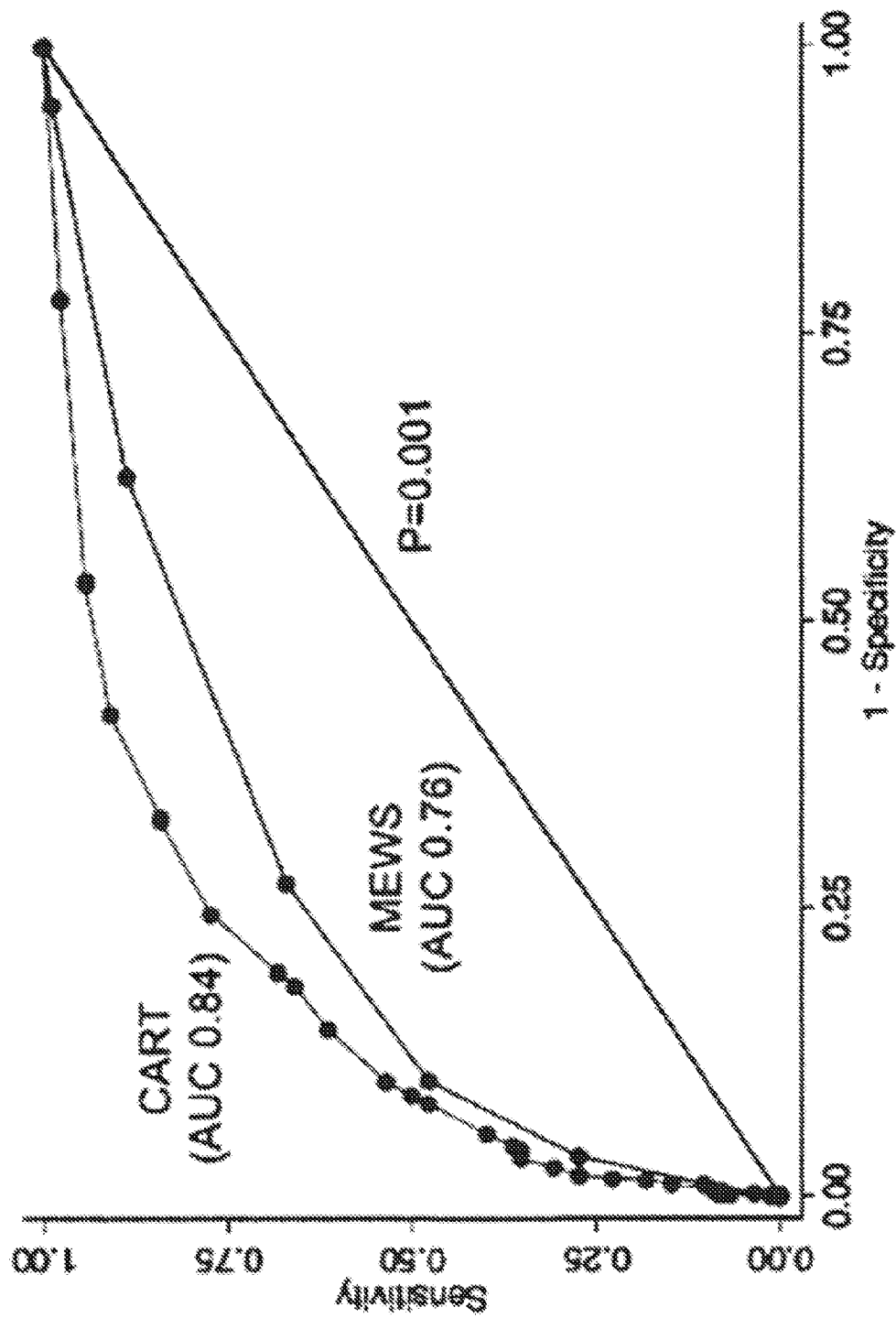
FIG. 10 illustrates a comparison between characteristic curves of the CART score and MEWS.

FIG. 10 compares the CART score and the MEWS, which shows the CART score was a better predictor of CA than MEWS (AUC 0.84 vs. 0.76; P=0.001). At a specificity of 89.9%, the CART score (cut-off >17) had a sensitivity of 53.4% compared to the MEWS (cut-off >4) sensitivity of 47.7%. For those CA patients detected by both systems at these thresholds, the CART score detected CA earlier than the MEWS (median 48 hours vs. 42 hours prior to the event; P=0.85), but this difference was not statistically significant. Compared to the MEWS at cut-off >4 (specificity 89.9%), the CART score at cut-off >20 had a specificity of 91.9% with the same sensitivity (47.7%). This would have resulted in 890 less patient calls over the study period (3648 vs. 4538 calls) while detecting the same number of CAs. In addition, the CART score predicted ICU transfer better than the MEWS (AUC 0.71 vs. 0.67; P<0.001). Both the CART score (AUC 0.84 vs. 0.71; P<0.001) and MEWS (AUC 0.76 vs. 0.67; P<0.001) predicted CA better than ICU transfer.

Mental Status Evaluation

1. Background

Altered mental status (AMS) may be used to describe a broad range of symptoms, including drowsiness, unresponsiveness, behavioral change, confusion or agitation. This broad diagnosis may include mild cognitive impairment, dementia, delirium, and coma. Patients with AMS have previously been shown to have a high admission rate, a prolonged length of hospital stay and a high mortality rate.

Delirium is one of the most common and clinically significant manifestations of AMS in the hospital. The four characteristics associated with a diagnosis of delirium are an acute and fluctuating course, attention deficits, disorganized thinking and talking, and fluctuating consciousness. The incidence of delirium is as high as 60% in the hospitalized elderly and its presence is a predictor for increased morbidity and mortality. However, recognition by medical and nursing staff of delirium on general wards is generally poor. It is estimated that 32% to 85% of delirium patients go unrecognized by physicians.

The present embodiments are easy-to-administer and can be used to detect early, acute changes in a patient's mental status in the hospital setting in a repeatable fashion over the course of a patient's hospitalization, without being influenced by differences in patient educational level, cultural background, or subjective evaluations of healthcare providers. As such, the present embodiments can supplement and improve detection of delirium by nurses, physicians, and/or other healthcare providers.

The Simon game was launched in 1978 by Milton Bradley and has ever since been a popular game that tests memory. The game is played with four differently colored blocks, which light up in a random order, after which the player must reproduce the order by pressing on the blocks. One more block lights up and is added to the color sequence after each correct reproduction of the color sequence by the player. A persons performance in this type of game can be influenced by, and thus indicative of, three cognitive functions: working memory capacity, attention, and sequence learning. The Simon game has been shown to have a weak to moderate positive correlation with the WAIS R digit span scores, which is a test of immediate auditory recall and freedom from distraction. Studies have shown that performance on the Simon game is unaffected by hearing loss. Although performance on the Simon game may be age and IQ related, the inventors have been unable to discover evidence that the Simon game is affected by educational level or cultural background. Even so, the Simon game would appear to be less influenced by these factors as compared to the Mini-Mental State Exam (MMSE) is a measure of the severity of cognitive impairment.

The following example of the present methods is configured for evaluating a patient's mental status or mental acuity that can be correlated with the MMSE and require less time to administer. The following example may also be more sensitive to small changes and less sensitive to education.

2. Exemplary Method

Figure 11A:
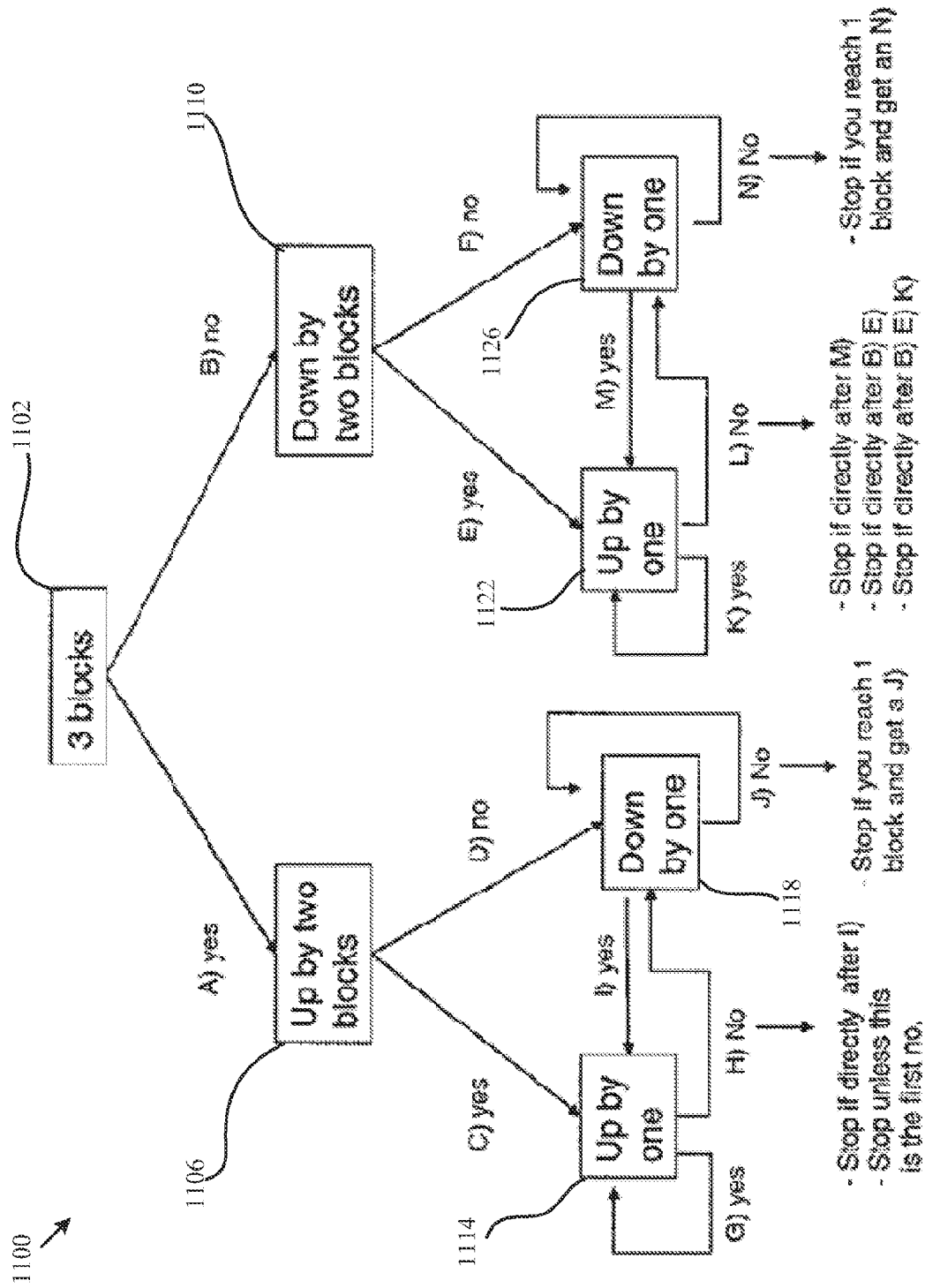
FIGS. 11A-B are flowcharts illustrating embodiments of the present methods for evaluating a patient's mental status.

FIG. 11A illustrates a flowchart of one embodiment of the present methods for evaluating a user's mental status. The game may be performed by and/or with devices such as those described in FIGS. 4-5. In the illustrated example, a user is initially presented 1102, via a display device, with a sequence of visual aids having three blocks, each having a different color and/or shape. The sequence of visual aids display on the display device for a predetermined period of time. When the sequence of visual aids disappear from the display device, the user is asked to enter a the sequence of visual aids that he/she is presented. If the user input sequence is identical to the sequence previously presented to him/her (the "yes" branch), the user is presented 1106 another sequence having five blocks. If the user input sequence is not identical to the sequence previously presented to him/her (the "no" branch), the user is presented 1110 another sequence having 1 block.

After step 1106, if the user input a sequence that is identical to the sequence previously presented to him/her, the length of the sequence is increased by one and another sequence of visual aids with increased length is presented 1114 to the user; or if the user input a sequence that is not identical to the sequence previously presented to him/her, the length of the sequence is decreased by one and another sequence of visual aids with decreased length is presented 1118 to the user. The above steps repeats until a stop criterion has been met.

After step 1110, if the user input a sequence that is identical to the sequence previously presented to him/her, the length of the sequence is increased by one and another sequence of visual aids with increased length is presented 1122 to the user; or if the user input a sequence that is not identical to the sequence previously presented to him/her, the length of the sequence is decreased by one and another sequence of visual aids with decreased length is presented 1126 to the user. The above steps repeats until a stop criterion has been met.

A stop criterion may be such that the length of a sequence of visual aid has been decreased to one. Another stop criterion may be such that a first input of a user is not identical to a sequence of visual indicators having a first length; a second input of a user is identical to a sequence of visual indicators have a second length that is less than the first length; and a third input of a user is not identical to a sequence of visual indicators having a third length that is greater than the second length (e.g., having a third length that is equal the first length). One of ordinary skill in the art may recognize other stop criteria according to the exemplary flow chart in FIG. 11A.

Figure 11B:
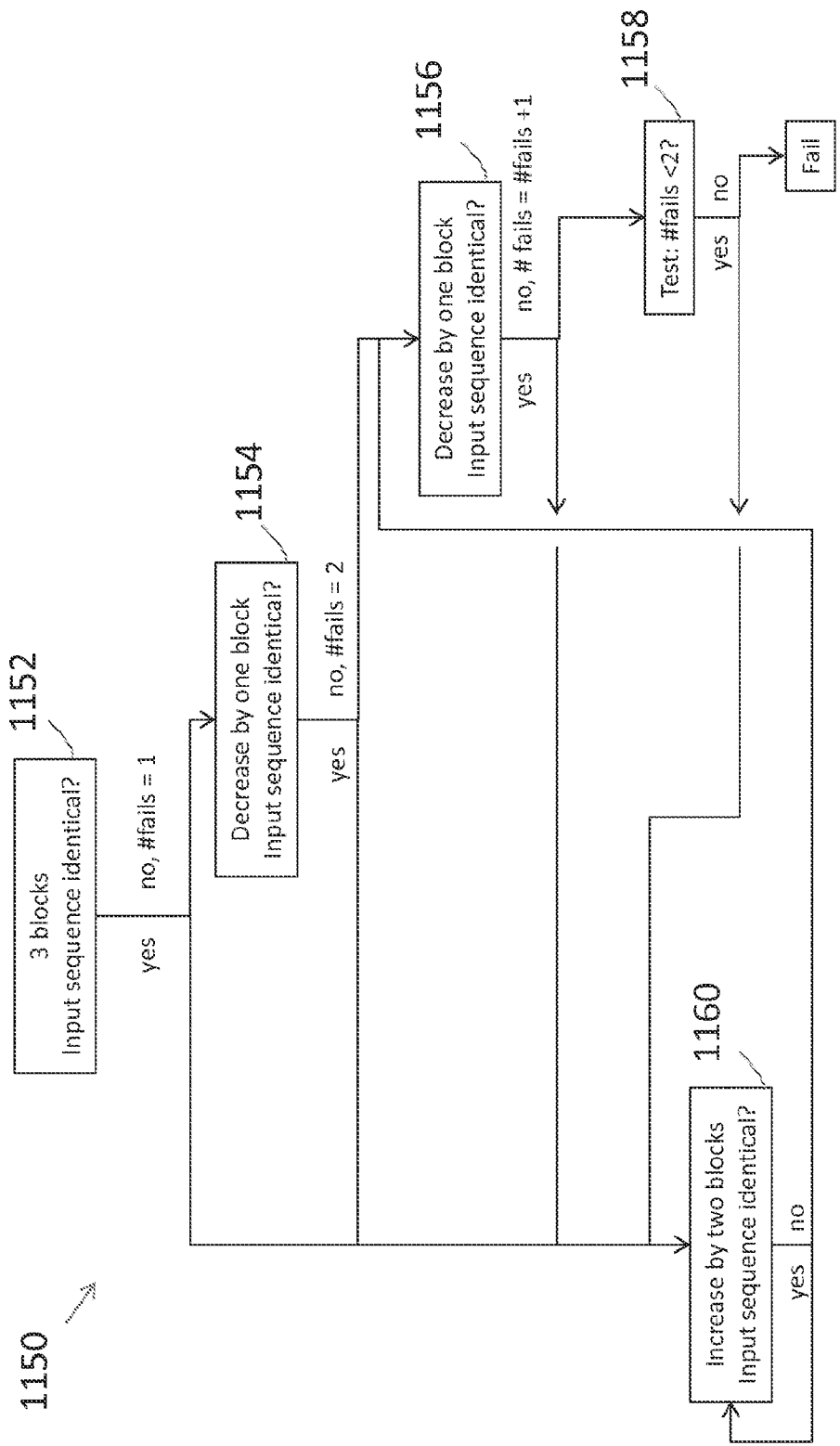

Another example of evaluating a patient's metal status is shown in embodiment 1150 of FIG. 11B. A similar game as described with respect to FIG. 11A may be played, however the patient may be evaluated by criteria described in FIG. 11B. A patient may be presented with three blocks at step 1152 and asked to input an identical sequence. If the patient succeeds then the block sequence is increased by two at step 1160 and the evaluation proceeds. If the patient fails at step 1160 then the evaluation continues at step 1156. If the patient fails at step 1152 then the number of fails is set to one and the sequence is decreased by one at step 1154 and the evaluation proceeds. If the patient is successful repeating the sequence at step 1154 then the evaluation proceeds to step 1160. If not, then the evaluation proceeds to step 1156 and the number of failures is set to 2. At step 1156, the block sequence is decreased by one and presented to the patient. If the patient inputs the correct sequence then the evaluation proceeds to step 1160. If not, then the number of failures is increased by one and the evaluation continues at step 1158 to determine if the number of failures is less than 2. If the number of failures is less than two then the evaluation proceeds to step 1160. If the number of failures is greater than or equal to two then the evaluation terminates at step 1158 in a failure.

Patient Acuity Rating

This section describes the Patient Acuity Rating (PAR) for evaluating a patient's mental acuity that may be incorporated into the methods and/or systems described above (e.g., for determining cardiac risk and/or a CART score).

1. Data

This study was conducted at The University of Chicago Hospitals, an academic, tertiary care facility with approximately 600 inpatient beds. Subjects involved both the clinicians who provided PAR scores and the patients upon whom the PAR scores and outcomes were based. The clinicians included internal medicine interns, residents, and attending physicians as well as midlevel providers (nurse practitioners or physician assistants). Clinicians were eligible for inclusion if they cared for patients on one of nine adult ward services between January and June 2008. They were included in the study if they consented to participate. Housestaff, with medicine attending supervision, covered patients on seven general medicine services, while midlevel practitioners, also with medicine attending supervision, covered patients on two hepatology and transplant services.

Providers were independently surveyed once per call cycle (every two to four days depending on the service) by study personnel regarding each of their patients, and instructed not to consult with other members of the team regarding their PAR score assignments. All patients for whom a participating clinician provided a PAR score were included in the analysis. Clinician subjects were carefully surveyed at the end of their work day, just prior to or immediately following their handover to the cross-covering physician, so as to minimize the risk that they might alter their plan and transfer a patient to the ICU based on the PAR score.

2. Rating

PAR is developed as a seven-point Likert scale to quantify clinician judgment regarding the stability of inpatients outside the intensive care unit (ICU). Prospective study of PAR's diagnostic accuracy for predicting impending clinical deterioration was performed in an academic tertiary care hospital. Providers were prospectively surveyed once per call-cycle on the day after patient admission and asked to rate each of their patients on their likelihood of suffering a cardiac arrest or being transferred to the ICU. The scale was anchored at both ends, with a PAR of 1 corresponding to extreme unlikelihood of suffering a cardiac arrest or requiring emergent ICU transfer within the next 24 hours and a PAR of 7 corresponding with extreme likelihood (FIG. 12). A score of 4 suggested neither likely nor unlikely to experience an event.

PAR scores were entered into a database (Excel, Microsoft Corporation, Redmond, Wash.) and then linked to patient demographic and outcome data obtained from hospital administrative databases. Weighted kappa statistics were used to evaluate inter-rater reliability. Ordinal trend testing was used to correlate the PAR with patient outcomes by provider. In addition, receiver operator characteristics (ROC) curves were constructed and area under the curve (AUC) calculated and compared among providers using paired chi-squared statistics. Sensitivities and specificities were determined for each theoretical PAR cutoff. Clustered multivariate logistic regression was used to adjust for provider, service and individual patient. All calculations were performed using a statistical software application (Stata, College Station, Tex.).

During the study period, 140/159 (88.1%) eligible clinicians consented to participate. Of these clinicians, 45 (32.1%) were intern physicians, 40 (28.6%) were resident physicians, 51 (36.4%) were attending physicians, and 4 (2.9%) were midlevel providers. They provided PAR scores on 1663 distinct patients over the course of 2019 separate admissions. FIG. 13 shows the patient and admission demographics grouped by the type of medical service: general medicine teaching or multispecialty non-teaching. Severity of Illness assignments were determined using All Patient Refined Diagnosis Related Group (APR-DRG) methodology, which incorporates features such as principle diagnosis at admission, co-morbidities, complications during admission, age and gender. The multispecialty patients were more likely to be male, have a higher severity of illness and die during the hospitalization when compared to general medicine patients.

A total of 6034 individual PAR scores from 3419 patient-days were obtained, which represented a response rate of 74.3%. The average PAR was 2.9±1.4. FIG. 14 shows the inter-rater reliability between providers. Weighted kappa statistics ranged from 0.32 (for interns and attendings) to 0.43 (for midlevels and attendings), representing moderate inter-rater reliability. No comparison was made between midlevel providers and interns or residents as these participants never cared for the same patients on the same day.

Figure 17:
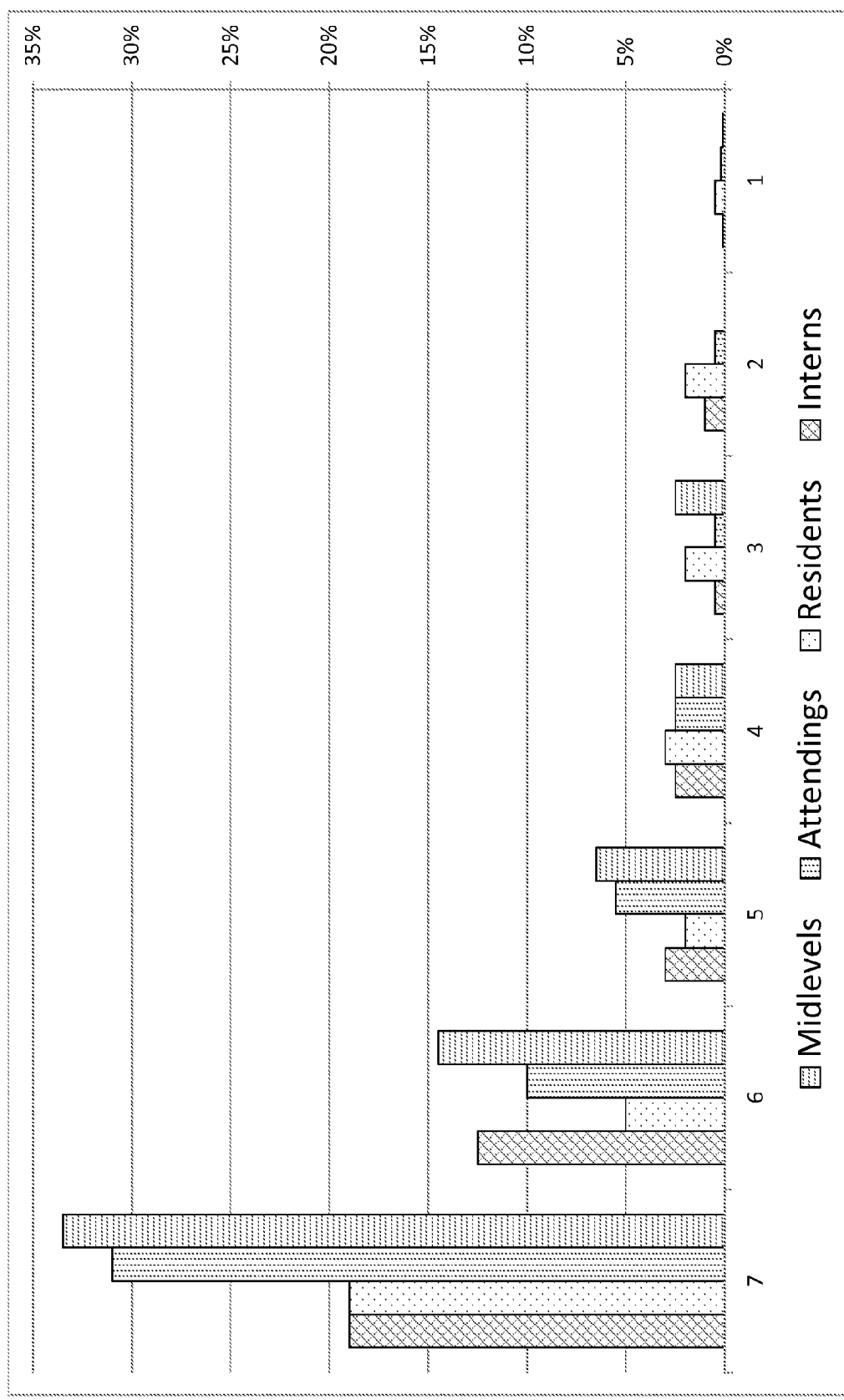
FIG. 17 illustrates percent of patient showing clinical deterioration to the point of cardiac arrest or ICU transfer by PAR and provider.

Seventy-four of the 3419 patient days (2.2%) ended in cardiac arrest or unplanned ICU transfer. The distribution of clinical deterioration by average PAR, along with sensitivity and specificity values, are shown in FIG. 15. Using a cut-off value of greater than or equal to five yielded a sensitivity of 62.2% and a specificity of 84.6%. Lowering the threshold to greater than or equal to four increased the sensitivity to 82.4% but decreased the specificity to 68.3%. This corresponded with an AUC of 0.82 [95% CI 0.77, 0.87] (FIG. 16). Provider specific AUC values ranged from a low of 0.69 [95% CI 0.59, 0.78] for residents to a high of 0.85 [95% CI 0.80, 0.90] for attendings (p=0.01). The remaining values were not statistically different from one another. FIG. 17 shows the provider specific percentage of patients deteriorating by PAR. The risk of clinical deterioration decreased in logarithmic fashion as the PAR decreased for all provider types (p<0.001). These results were confirmed using multivariate logistic regression adjusting for provider, service, and individual patient (data not shown). In addition, we found no significant differences in AUC values between attendings in terms of years in practice or specialty, however the study was not powered to detect such differences.

Electronic Health Records

This section describes using a patient's electronic health record (EHR) to determine a likelihood that the patient will experience a cardiac arrest that may be incorporated into the methods and/or systems described above (e.g., for determining cardiac risk and/or a CART score). An examination of the patient's electronic health record may prompt a caregiver to initiate the mental tests described above. Alternatively, when calculating an aggregate score for the patient, a calculation may take into account data from the patient's EHR in addition to the patient's mental status.

Routinely collected vital signs (respiratory rate, blood pressure, heart rate, oxygen saturation, use of supplemental oxygen, temperature, and/or mental status) and/or laboratory values (white cell count, hemoglobin, platelets, sodium, potassium, chloride, bicarbonate, anion gap, blood urea nitrogen, and/or glucose) may be collected from an EHR system, such as EPIC; Verona, Wis., or the like, to be used as potential predictor variables for cardiac arrest (CA). Patient age, whether they had previously been in an ICU during the current hospitalization, and/or other demographic characteristics may be collected from the EHR or other administrative databases. Mental status may be collapsed from four fields corresponding to orientation, level of consciousness, motor response, and responsiveness into one score (alert, responsive to voice, responsive to pain, and unresponsive (AVPU)) for each observation. According to one embodiment, the time that laboratory results were available in the EHR may be used as the observation time for these values in the dataset.

A prediction model may be used to select patients from the EHR at high risk of cardiac arrest. These patients may then be targeted for intervention before a cardiac arrest occurs, such as through an automated call or a critical care consult. The prediction model may also separate out intensive care unit (ICU) transfer patients from cardiac arrest (CA) patients. For example, decreasing temperature may be a significant predictor of cardiac arrest but not ICU transfer, while hypoxia may be significantly associated with ICU transfer but not cardiac arrest. This separation is useful because caregivers may be more apt to recognize patients who have certain abnormalities (e.g. hypoxia) and so these patients are appropriately transferred to the ICU, while patients with evidence of other types of physiologic deterioration (e.g. hypothermia) may not be recognized to the same degree.

When reading values from an EHR, the prediction model may take into consideration blood urea nitrogen, anion gap, potassium, hemoglobin, white blood cell count, and/or platelet count, which are all predictors of cardiac arrest. Each of these values may be assigned a weighted value in a final score for the patient. The prediction model may also consider Acute Physiology and Chronic Health Evaluation (APACHE) II scores, potassium values, creatinine values, white blood cell counts, hematocrit values, Pneumonia Severity Index scores, and/or Ranson's criteria.

By implementing a prediction model that accesses data in electronic health records, real-time feedback may be provided to nurses and physicians regarding how likely their patients are to suffer a cardiac arrest. This is useful particularly with the increasing number of patient hand-offs that occur in many hospitals today, as providers often have less first-hand knowledge about the patients they are caring for. Automatic score generation by the EHR may also decrease the error rate in score calculation. Furthermore, the prediction model may be used to send automatic notifications to physicians and the hospital's RRT, circumventing the "failure to call" problem. Thus, the EHR provides a medium to improve both the risk stratification of patients and the notification of caregivers. A hospital may then individualize their response to patients based, in part, on available resources, including calls to the RRT, critical care consults, and increased frequency of monitoring.

A table providing regression coefficients and p-values for variables in the prediction model for cardiac arrests according to one embodiment of the prediction model is shown in Tables 4A. Table 4B lists regression coefficients and p-values for variables in the prediction model for separating ICU transfers according to one embodiment of the prediction model.

TABLE 4A

Regression coefficients and p-values for variables in a cardiac-arrest model

| | Cardiac arrest | | | |
|---|---|---|---|---|
| Variable | Coefficient | Lower 95% CI | Upper 95% CI | p-value |
| Time (hours) | 0.00 | −0.002 | 0.001 | 0.418 |
| Prior ICU stay (1 = Yes, 0 = No) | 1.37 | 0.982 | 1.751 | 0.000 |

TABLE 4A-continued

Regression coefficients and p-values for variables in a cardiac-arrest model

| | Cardiac arrest | | | |
|---|---|---|---|---|
| Variable | Coefficient | Lower 95% CI | Upper 95% CI | p-value |
| Heart rate (beats/min) | 0.03 | 0.022 | 0.044 | 0.000 |
| Diastolic blood pressure (mmHg) | −0.02 | −0.034 | −0.004 | 0.011 |
| Respiratory rate (breaths/min) | 0.14 | 0.095 | 0.192 | 0.000 |
| Oxygen saturation (%) | 0.07 | −0.021 | 0.154 | 0.137 |
| Temperature (° C.) | −0.31 | −0.585 | −0.028 | 0.031 |
| Mental status (AVPU) | 0.43 | −0.342 | 1.205 | 0.274 |
| On room air (1 = Yes, 0 = No) | −0.64 | −1.186 | −0.087 | 0.023 |
| Age (years) | 0.03 | 0.014 | 0.039 | 0.000 |
| BUN (mg/dL) | 0.01 | 0.003 | 0.018 | 0.005 |
| Anion gap (mEq/L) | 0.13 | 0.093 | 0.164 | 0.000 |
| Hemoglobin (g/dL) | −0.17 | −0.292 | −0.045 | 0.007 |
| Platelet count (K/uL) | −0.002 | −0.004 | −0.001 | 0.007 |
| Potassium (mEq/L) | 0.17 | −0.159 | 0.504 | 0.307 |
| White blood cell count (K/uL) | 0.01 | 0.002 | 0.016 | 0.011 |

TABLE 4B

Regression coefficients and p-values for variables in ICU-transfer model

| | ICU transfer | | | |
|---|---|---|---|---|
| Variable | Coefficient | Lower 95% CI | Upper 95% CI | p-value |
| Time (hours) | 0.00 | −0.003 | −0.002 | 0.000 |
| Prior ICU stay (1 = Yes, 0 = No) | 0.12 | 0.016 | 0.225 | 0.024 |
| Heart rate (beats/min) | 0.04 | 0.032 | 0.037 | 0.000 |
| Diastolic blood pressure (mmHg) | −0.01 | −0.010 | −0.004 | 0.000 |
| Respiratory rate (breaths/min) | 0.14 | 0.124 | 0.146 | 0.000 |
| Oxygen saturation (%) | −0.05 | −0.058 | −0.034 | 0.000 |
| Temperature (° C.) | −0.01 | −0.060 | 0.051 | 0.868 |
| Mental status (AVPU) | 1.16 | 1.038 | 1.279 | 0.000 |
| On room air (1 = Yes, 0 = No) | −0.32 | −0.414 | −0.215 | 0.000 |
| Age (years) | 0.02 | 0.012 | 0.017 | 0.000 |
| BUN (mg/dL) | 0.01 | 0.010 | 0.014 | 0.000 |
| Anion gap (mEq/L) | 0.07 | 0.055 | 0.080 | 0.000 |
| Hemoglobin (g/dL) | −0.01 | −0.034 | 0.013 | 0.368 |
| Platelet count (K/uL) | −0.001 | −0.001 | −0.001 | 0.000 |
| Potassium (mEq/L) | 0.13 | 0.058 | 0.208 | 0.001 |
| White blood cell count (K/uL) | 0.01 | 0.005 | 0.010 | 0.000 |

A predictive model for predicting cardiac arrest or an upcoming need for ICU transfer may be constructed based on the regression coefficients listed in Table 4A or 4B, respectively, for those variables found to be predictive (p-value<0.05). For example, a score (e.g., a CART2 score) indicative of a patient's risk of cardiac arrest may be calculated according to 4*(the weighted linear sum of the patient's values for each of the variables+20) (Equation 1), wherein the weighting coefficients are determined through regression modeling. In one example, the weighting coefficients are the weighting coefficients provided in Table 4A or 4B. The multiplicative factor (4) and the added offset (20*4) may be selected to shift and scale the score into a convenient range selected for ease of interpretation. The multiplicative factor and offset were selected in the present embodiment to scale the cardiac arrest score onto the range [0,60], for convenience. Some patient scores may fall outside of the target scaling range; and most patients will yield a score in this range.

Those of ordinary skill in the art will appreciate that the weighting coefficients may be adjusted over a range without destroying the predictive value of a predictive score. As an example, each coefficient listed in Table 4A or 4B may be varied within the lower and upper 95% confidence limits (CL) to yield a score within 95% of the score predicted using the coefficient values listed. Each coefficient may be varied outside of these 95% confidence limits, although the predictive value of the score for patient care purposes may be reduced.

Score thresholds and ranges indicating, for example, low, intermediate, high, or very high risks of a cardiac arrest or an upcoming need for ICU transfer may be determined, depending on the choice of score rescaling. For example, a score determined according to Equation 1 would indicate a low risk if the score fell into the range less than approximately 10-15 (e.g., score<12.5), an intermediate risk if the score fell into the range between approximately 10-15 and approximately 15-20 (e.g., 12.5<score<17.5), a high risk if the score fell into the range between approximately 15-20 and approximately 25 (e.g., 17.5<25), and a very high risk if the score fell into the range above approximately 25 (e.g., 25<score) (see FIG. 7). The numerical values of the thresholds will depend on the scaling function, and one of ordinary skill in the art will understand how to rescale the thresholds to accommodate a different score scaling function.

Without limiting the subject matter described, for example, a patient's risk of cardiac arrest or an upcoming need for ICU transfer may be calculated using a weighted linear sum comprising all of the variables and coefficients listed in Table 4A or 4B. As another example, a patient's risk of cardiac arrest or an upcoming need for ICU transfer may be calculated using a weighted linear sum consisting of all of the variables and coefficients listed in Table 4A or 4B. As yet another example, a patient's risk of cardiac arrest or an upcoming need for ICU transfer may be calculated using a weighted linear sum consisting of a subset of the variables and coefficients listed in Table 4A or 4B. Such a subset may consist of, for example, those variables that have been shown to be predictive based on a p-value<0.05. For example, a patient's risk of cardiac arrest may be calculated using a weighted linear sum consisting of prior ICU stay, heart rate, diastolic blood pressure, respiratory rate, temperature, the use of in-room oxygen, age, BUN, anion gap, hemoglobin, platelet count, and white blood cell count. For example, a patient's risk of or an upcoming need for ICU transfer may be calculated using a weighted linear sum consisting of time, prior ICU stay, heart rate, diastolic blood pressure, respiratory rate, oxygen saturation, temperature, mental status, the use of in-room oxygen, age, BUN, anion gap, platelet count, potassium, and white blood cell count.

When this prediction model is implemented, sensitivity and specificity for identifying patients who suffered cardiac arrest at different cut-points may be those shown in Table 5.

TABLE 5

Sensitivity and specificity for identifying patients who suffered cardiac arrest at different cut-points for the prediction (derived) model and for the ViEWS model

| | Sensitivity (%) | Specificity (%) |
|---|---|---|
| Derived model | | |
| >49 | 81 (72-88) | 82 (82-83) |
| >50 | 77 (68-85) | 86 (86-86) |
| >51 | 71 (61-79) | 89 (89-89) |
| >52 | 66 (57-75) | 92 (92-92) |
| >53 | 65 (55-74) | 93 (93-93) |
| >54 | 60 (50-69) | 95 (95-95) |

TABLE 5-continued

Sensitivity and specificity for identifying patients who suffered cardiac arrest at different cut-points for the prediction (derived) model and for the ViEWS model

|  | Sensitivity (%) | Specificity (%) |
|---|---|---|
| >55 ViEWS | 56 (46-66) | 96 (96-96) |
| >7 | 72 (62-80) | 73 (73-73) |
| >8 | 60 (50-69) | 85 (85-85) |
| >9 | 41 (32-51) | 93 (93-93) |
| >10 | 29 (21-39) | 97 (97-97) |

This embodiment of the present model was compared to the VitalPAC™ Early Warning Score (ViEWS), the most accurate risk score from a recent comparison study [Prytherch (2010)], using the area under the receiver operating characteristic curve (AUC) and was validated using three-fold cross validation. The model detected cardiac arrest (AUC 0.88 vs. 0.78; P<0.001) and ICU transfer (AUC 0.77 vs. 0.73; P<0.001) more accurately than the ViEWS when using each patient's highest score, and results were similar when using whether the event occurred within 24 hours as the definition for model accuracy (Table 6). At a specificity of 93%, the prediction model had a higher sensitivity than the ViEWS for CA patients (65% vs. 41%). The model thus provides a validated a prediction tool for ward patients that can simultaneously predict the risk of CA and ICU transfer. The prediction model is more accurate than the ViEWS and could be implemented in the EHR to alert caregivers with real-time information regarding patient deterioration.

TABLE 6

Areas under the receiver operating characteristic curves (AUCs) for cardiac arrest or ICU transfer for the derived model and ViEWS

| | Score | | |
|---|---|---|---|
| Outcome | Cardiac arrest model[a] | ICU transfer model[a] | ViEWS |
| Ever experienced event | | | |
| Cardiac arrest | 0.88 (0.84-0.91) | — | 0.78 (0.73-0.83) |
| ICU transfer | — | 0.77 (0.76-0.78) | 0.73 (0.72-0.74) |
| Experienced event within 24 hours | | | |
| Cardiac arrest | 0.88 (0.88-0.89) | — | 0.74 (0.72-0.75) |
| ICU transfer | — | 0.76 (0.76-0.76) | 0.73 (0.72-0.73) |

*Score for cardiac arrest and ICU models were derived from the cardiac arrest and ICU transfer portions of the multinomial logistic regression model.

Figure 18:
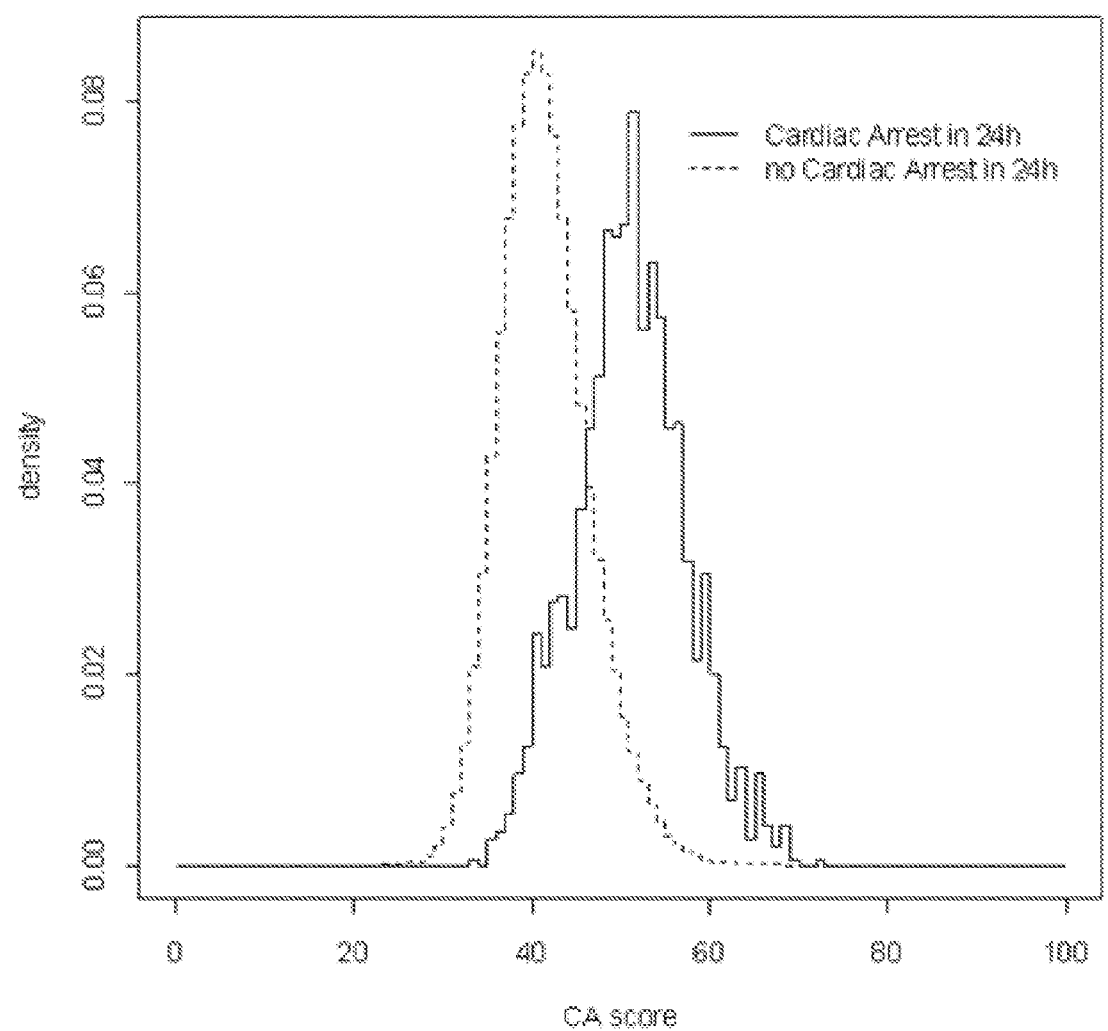
FIG. 18 illustrates a graph of empirical density plots of a cardiac arrest score for two groups of patients who did and did not suffer a cardiac arrest.

Profiles of patients experiencing cardiac arrest and not experiencing cardiac arrest based on the patients' score generated by the above-described prediction model are shown in FIG. 18. The empirical data of FIG. 18 illustrates a statistical significance that patients with higher scores are more likely to experience a cardiac arrest.

Comparison of Scoring Methods

Because the systems described above in the Background Section represent recent advances, many have not been directly compared to one another in the same dataset. Therefore, a database of ward admissions from November 2008 until August 2011 consisting of both medical and surgical patients was used to compare the different early warning scores described above. The patient population, in brief, consisted of all patients on the ward from a single urban academic center in the United States. The hospital has had a rapid response team in place since 2008, which is led by a critical care nurse and is separate from the team that responds to cardiac arrests. Respiratory therapy also responds to team activations and a hospitalist attending physician and/or pharmacist are available upon request.

Recently developed or validated single parameter (i.e. Cretikos et al.), multiple parameter (i.e. Bleyer et al.), and aggregate weighted (i.e. Tarassenko et al., ViEWS, SEWS) risk scores, as well as the present CART score, were comparted to previously validated systems that are commonly used (i.e. the MERIT criteria and MEWS). Not all of the recently developed systems could be compared because room air oxygen saturation, body mass index, urine output, and accurate determination of patients admitted to the surgical service were not available. In addition, some aspects of the MERIT criteria were not captured in the available dataset, such as a drop in Glasgow Coma Scale score, the presence of seizures, and airway emergencies.

Ward vital signs were extracted from electronic health record (EPIC; Verona, Wis.), and each of the early warning scores was calculated for every simultaneous ward vital sign set in the entire dataset. If a necessary vital sign was missing, then the most recent value was carried forward. In addition, if there were no previous values then a median value was imputed. Cardiac arrest was determined using a prospectively validated quality improvement database, and ICU transfer and mortality were determined using administrative databases. Accuracy was calculated using the AUC, sensitivity, and specificity for detecting cardiac arrest, ICU transfer, mortality, and a composite outcome of any of these events using each patient's highest score prior to the event or during their entire admission for those who did not experience an event. Ward patients transferred to the ICU from the operating room were not counted as an ICU transfer event. Of note, the CART score was developed to detect cardiac arrest using an older version of these data that account for approximately 80% of the patients in this updated dataset.

During the study period, there were 59,643 admissions with ward vital signs, including 109 ward cardiac arrests, 291 deaths within 24 hours of a ward vital sign, and 2655 ward to ICU transfers. The included patients had a mean age of 55±18 years, 56% were female, 43% were Black, 36% were White, and 34% underwent surgery during the hospitalization. Results from the early warning score comparisons are shown in Table 7, separated by outcome.

TABLE 7

Accuracy of track and trigger systems for different outcomes

| Track and trigger system | Cardiac arrest | ICU transfer | Mortality | Composite |
|---|---|---|---|---|
| MERIT | 0.63 (0.59-0.68) | 0.64 (0.63-0.65) | 0.74 (0.71-76) | 0.64 (0.64-0.65) |
| Modified MERIT | 0.69 (0.65-0.74) | 0.69 (0.68-0.70) | 0.79 (0.76-0.81) | 0.70 (0.69-0.70) |
| Multiple parameter, from Bleyer et al. | 0.73 (0.68-0.78) | 0.72 (0.71-0.73) | 0.84 (0.82-0.87) | 0.73 (0.72-0.74) |

TABLE 7-continued

Accuracy of track and trigger systems for different outcomes

| Track and trigger system | Cardiac arrest | ICU transfer | Mortality | Composite |
| --- | --- | --- | --- | --- |
| Centile-based, from Tarassenko et al. | 0.70 (0.65-0.76) | 0.71 (0.69-0.72) | 0.83 (0.80-0.86) | 0.72 (0.70-0.73) |
| MEWS | 0.76 (0.71-0.81) | 0.74 (0.73-0.75) | 0.87 (0.84-0.89) | 0.75 (0.74-0.76) |
| SEWS | 0.76 (0.71-0.81) | 0.75 (0.74-0.76) | 0.88 (0.86-0.90) | 0.76 (0.75-0.77) |
| ViEWS | 0.77 (0.72-0.82) | 0.73 (0.72-0.75) | 0.88 (86-0.91) | 0.75 (0.74-0.76) |
| CART score | 0.83 (0.79-0.86) | 0.77 (0.76-0.78) | 0.88 (0.86-0.90) | 0.78 (0.77-0.79) |

*Data are shown as area under the receiver operating characteristic curve (95% confidence interval).
**Abbreviations: ICU, intensive care unit; MERIT, medical early response intervention and therapy; SEWS, standardized early warning score; MEWS, modified early waning score; ViEWS, VitalPAC ™ early warning score; CART, cardiac arrest risk triage The various scoring methods were found to have a wide range of accuracy, both across outcomes for a given system and across systems. In general, mortality resulted in the highest AUCs, while ICU transfer resulted in the lowest. Overall, the aggregate weighted scoring systems outperformed the other systems for most outcomes, with the SEWS, MEWS, ViEWS and CART score being the most accurate. In addition, the modified MERIT criteria described by Cretikos were more accurate than the original MERIT criteria for all outcomes. While the ViEWS, CART, MEWS and SEWS were somewhat similar in performance across the outcomes, the CART score had the highest AUC for cardiac arrest (0.83), ICU transfer (0.77), and the composite outcome (0.78), while the CART score, ViEWS and SEWS all had the same AUC for mortality (0.88). The ViEWS was the second most accurate system for detecting cardiac arrest (0.77), while the SEWS was the second most accurate for ICU transfer (AUC 0.75) and the composite outcome (AUC 0.76). Since the CART score was derived using many of the patients from this dataset, the analysis for the CART score was repeated using only those patients not in the original study (i.e. prospective validation), which yielded similar results (AUCs of 0.86, 0.76, 0.87, and 0.77 for cardiac arrest, ICU transfer, mortality, and the composite outcome, respectively). Sensitivity and specificity values at cut-points closest to 85%, 90%, and 95% specificity for the four most accurate systems for detecting cardiac arrest are shown in Table 8.

TABLE 8

Sensitivity and specificity at selected cut-points for the most accurate track and trigger systems for identifying cardiac arrest patients

| Track and trigger system cut-point | Sensitivity | Specificity |
| --- | --- | --- |
| SEWS | | |
| >3 | 55% | 85% |
| >4 | 38% | 94% |
| >5 | 19% | 97% |
| MEWS | | |
| >3 | 67% | 80% |
| >4 | 39% | 91% |
| >5 | 20% | 96% |
| ViEWS | | |
| >8 | 60% | 83% |
| >9 | 41% | 91% |
| >10 | 29% | 95% |
| CART | | |
| >16 | 61% | 84% |
| >20 | 49% | 90% |
| >24 | 35% | 95% |

*Abbreviations: SEWS, standardized early warning score; MEWS, modified early waning score; ViEWS, VitalPACTM early warning score; CART, cardiac arrest risk triage At a specificity threshold of approximately 90%, the CART score had a sensitivity of 49%, compared to the ViEWS (41%), MEWS (39%), and the centile-based system (35%, data not shown). The SEWS and the multiple parameter system by Bleyer and colleagues did not have cut-offs near this level of specificity. The MERIT criteria had a sensitivity and specificity of 45% and 82% for detecting cardiac arrest compared to the modified criteria proposed by Cretikos, which had a sensitivity of 54% and specificity of 84%.

The number of published risk scores for ward patients has grown rapidly over the past decade, in large part due to the popularity of rapid response systems. Aggregate weighted early warning scores, specifically the ViEWS, SEWS, MEWS, and CART score, were more accurate than other types of scoring systems for detecting cardiac arrest, mortality, ICU transfer and a composite outcome in the dataset utilized. Hospitals seeking to implement an aggregate weighted scoring system should consider the available variables, possible calculation methods, and system resources when selecting the appropriate tool for their setting.

An important part of the process of implementing a physiologic track and trigger system, especially an aggregate weighted system, is determining how the score will be calculated. Options include calculation by hand, using a calculator or handheld device developed specifically for the scoring system, and using the electronic medical record. Manual calculation, with or without a calculator, is the most commonly used method and the least expensive to implement. However, studies suggest that calculation errors are not uncommon. Pre-programmed applications decrease these errors but still require manual entering of the data, which can be redundant to workflow and error prone in its own right. Completely automated systems such as those integrated into electronic medical records are likely to be the least labor intensive from the clinician standpoint and least error prone. Moreover, they have the potential to incorporate other patient data such as demographic characteristics, location, and laboratory values and even be tied into automated notification systems. However, these systems require institutional resources to implement and may not be an option for most hospitals, especially those with paper-based medical records.

As demonstrated above, the reported accuracy of a scoring system will depend in large part on the outcome chosen for validation. Therefore, comparison of systems requires a consistency in outcome selection. While mortality is the easiest to predict, as evidenced by the higher AUCs, it may not be the most useful since many deaths in the hospital are fully expected, and detecting those events may not be necessary or helpful. However, most studies of early warning scores have not omitted DNR patients from their analyses. Reasons for this may include difficulty in identifying such patients in large datasets, the inability to determine the exact time when the goals in patient care transition from life-saving (when early warning scores might be beneficial) to comfort (when risk scores would not be useful), the thought that some DNR patients still desire other life-saving interventions, and previous studies suggesting that rapid response teams can improve some aspects of end-of-life care. ICU transfer represents the most common outcome and thus results in the highest statistical power but is the least generalizable given the heterogeneous criteria for admission, resulting in the lowest AUCs. Moreover, it is, by definition, an event already recognized by hospital staff, albeit late on some occasions. In addition, criteria for ICU admission in some hospitals may include vital sign cut-offs, and so scores derived or validated in such hospitals would be affected by these criteria. Similar to mortality, cardiac arrest has the benefit of being objectively defined. However, unlike mortality, it is always worth identifying and preventing, if only to institute a DNAR order in some cases. As such, a cardiac arrest on the floor always represents a failure of the current system and thus may be the most clinically relevant of the outcomes to use for derivation and validation. However, reporting all four outcomes in future studies would allow readers to draw their own conclusions about relevant outcomes for their own practice. Some authors have stated that the original early warning scores were not developed to be highly accurate predictors of any specific outcome due to the many confounding events that occur during a hospitalization. In addition, as described above, investigators have also used the distribution of vital signs to determine cut-offs for risk scores, arguing that deriving models based on outcomes, when used prospectively, will disadvantage those patients who would have been previously "salvaged" by the vital sign monitoring system that had been previously in use in the development dataset.

Older age is a known risk factor for cardiac arrest and death and is often included in risk scores used in the ICU. However, age is rarely included in current risk scores for ward patients. Several studies have shown that the increased risk of adverse outcomes associated with increased age is independent of vital sign derangements, and the inclusion of age has been shown to improve the accuracy of risk scores, although to varying degrees. Some concerns raised about including age in early warning scores are ethical in nature, and including age could make it less likely for younger patients with vital sign abnormalities to be identified. It is unknown to what degree this would occur, given that cardiac arrest and death are much more common in older age groups. In addition, it is unknown whether vital signs prior to these events differ between younger and older patients given the increased use of beta-blockers in older patients and the physiologic changes that occur with aging.

The most-important unanswered question is whether early warning scores improve outcomes. To definitively answer this question, a large randomized trial would be needed that used a well-validated risk score, and even then separating the effects of the specific risk score utilized in the study from the intervention would be difficult. Many before and after studies have been published highlighting the usefulness of early warning scores (usually concurrently implemented with rapid response systems), including improved vital sign documentation and improved patient outcomes. However, these findings have not been universal, and it is currently unclear whether early warning scores improve important patient outcomes such as hospital-wide cardiac arrest and mortality rates or decrease costs. Importantly, delayed response has been identified as one of the strongest predictors of mortality and unexpected ICU transfer in patients evaluated by the rapid response team. Future efforts to improve the evidence base for early warning scores are needed, as are methods to improve adherence to vital sign documentation and rapid response system activation after they are implemented. Automated implementation with built-in notification, as described above, is likely to help but this remains to be demonstrated, and the cost effectiveness needs to be studied. Finally, pairing the different risk strata to specific levels of interventions, such as increased monitoring, consultation by the ICU team, and automatic calls to the RRT is essential, and different workflows have been proposed.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

[1] Berlot G, Pangher A, Petrucci L, Bussani R, Lucangelo U. Anticipating events of in-hospital cardiac arrest. Eur J Emerg Med. 2004; 11(1):24-8.
[2] Hodgetts T J, Kenward G, Vlachonikolis I G, Payne S, Castle N. The identification of risk factors for cardiac arrest and formulation of activation criteria to alert a medical emergency team. Resuscitation. 2002; 54(2):125-31.
[3] Cretikos M, Chen J, Hillman K, Bellomo R, Finfer S, Flabouris A, et al. The objective medical emergency team activation criteria: a case-control study. Resuscitation. 2007; 73(1):62-72.
[4] Merchant R M, Yang L, Becker L B, Berg R A, Nadkarni V, Nichol G, et al. Incidence of treated cardiac arrest in hospitalized patients in the United States. Crit Care Med. 2011; 39:2401-2406.
[5] Excellence: NIfHaC. Acutely ill patients in hospital: recognition of and response to acute illness in adults in hospital. NICE clinical guideline No. 50. London. 2007.
[6] Jenkins P F, Thompson C H, Barton L L, Jenkins P F, Thompson C H, Barton L L. Clinical deterioration in the condition of patients with acute medical illness in Australian hospitals: improving detection and response. Medical Journal of Australia. 2011; 194(11):596-8.

[7] Subbe C P. Better ViEWS ahead? It is high time to improve patient safety by standardizing Early Warning Scores. Resuscitation. 2010; 81(8):923-4.

[8] Smith G B, Prytherch D R, Schmidt P E, Featherstone P I. Review and performance evaluation of aggregate weighted 'track and trigger' systems. Resuscitation. 2008; 77(2):170-9.

[9] Smith G B, Prytherch D R, Schmidt P E, Featherstone P I, Higgins B. A review, and performance evaluation, of single-parameter "track and trigger" systems. Resuscitation. 2008; 79(1):11-21.

[10] Cuthbertson B H, Boroujerdi M, McKie L, Aucott L, Prescott G. Can physiological variables and early warning scoring systems allow early recognition of the deteriorating surgical patient? Crit Care Med. 2007; 35(2):402-9.

[11] Cuthbertson B H, Boroujerdi M, Prescott G. The use of combined physiological parameters in the early recognition of the deteriorating acute medical patient. J R Coll Physicians Edinb. 2010; 40(1):19-25.

[12] Churpek M M, Yuen T C, Huber M T, Park S Y, Hall J B, Edelson D P. Predicting cardiac arrest on the wards: a nested case-control study. Chest. 2012; 141(5):1170-6.

[13] Edelson D P, Litzinger B, Arora V, Walsh D, Kim S, Lauderdale D S, et al. Improving in-hospital cardiac arrest process and outcomes with performance debriefing. Arch Intern Med. 2008; 168(10):1063-9.

[14] Efron B. Logistic-Regression, Survival Analysis, and the Kaplan-Meier Curve. Journal of the American Statistical Association. 1988; 83(402):414-25.

[15] Ingram D D, Kleinman J C. Empirical Comparisons of Proportional Hazards and Logistic-Regression Models. Statistics in Medicine. 1989; 8(5):525-38.

[16] Gibbons R D, Duan N, Meltzer D, Pope A, Penhoet E D, Dubler N N, et al. Waiting for organ transplantation: results of an analysis by an Institute of Medicine Committee. Biostatistics. 2003; 4(2):207-22.

[17] Prytherch D R, Smith G B, Schmidt P E, Featherstone P I. ViEWS—Towards a national early warning score for detecting adult inpatient deterioration. Resuscitation. 2010; 81(8):932-7.

[18] Churpek M M, Yuen T C, Park S Y, Meltzer D O, Hall J B, Edelson D P. Derivation of a cardiac arrest prediction model using ward vital signs*. Crit Care Med. 2012; 40(7):2102-8.

[19] Steyerberg E W, Harrell F E, Jr., Borsboom G J, Eijkemans M J, Vergouwe Y, Habbema J D. Internal validation of predictive models: efficiency of some procedures for logistic regression analysis. J Clin Epidemiol. 2001; 54(8):774-81.

[20] Bleyer A J, Vidya S, Russell G B, Jones C M, Sujata L, Daeihagh P, et al. Longitudinal analysis of one million vital signs in patients in an academic medical center. Resuscitation. 2011; 82(11):1387-92.

[21] Escobar G J, LaGuardia J C, Turk B J, Ragins A, Kipnis P, Draper D. Early detection of impending physiologic deterioration among patients who are not in intensive care: development of predictive models using data from an automated electronic medical record. J Hosp Med. 2012; 7(5):388-95.

[22] Knaus W A, Draper E A, Wagner D P, Zimmerman J E. APACHE II: a severity of disease classification system. Crit Care Med. 1985; 13(10):818-29.

[23] Fine M J, Auble T E, Yealy D M, Hanusa B H, Weissfeld L A, Singer D E, et al. A prediction rule to identify low-risk patients with community-acquired pneumonia. N Engl J Med. 1997; 336(4):243-50.

[24] Ranson J H, Rifkind K M, Roses D F, Fink S D, Eng K, Spencer F C. Prognostic signs and the role of operative management in acute pancreatitis. Surg Gynecol Obstet. 1974; 139(1):69-81.

[25] Kellett J, Kim A. Validation of an abbreviated Vitalpac Early Warning Score (ViEWS) in 75,419 consecutive admissions to a Canadian regional hospital. Resuscitation. 2012; 83(3):297-302.

[26] Prytherch D R, Smith G B, Schmidt P, Featherstone P I, Stewart K, Knight D, et al. Calculating early warning scores—a classroom comparison of pen and paper and hand-held computer methods. Resuscitation. 2006; 70(2): 173-8.

[27] Subbe C P, Gao H, Harrison D A. Reproducibility of physiological track-and-trigger warning systems for identifying at-risk patients on the ward. Intensive Care Med. 2007; 33(4):619-24.

[28] Hillman K, Chen J, Cretikos M, Bellomo R, Brown D, Doig G, et al. Introduction of the medical emergency team (MET) system: a cluster-randomised controlled trial. Lancet. 2005; 365(9477):2091-7.

[29] Marshall S D, Kitto S, Shearer W, Wilson S J, Finnigan M A, Sturgess T, et al. Why don't hospital staff activate the rapid response system (RRS)? How frequently is it needed and can the process be improved? Implement Sci. 2011; 6:39.

[30] U.S. patent application Ser. No. 12/036,285
[31] UK Patent Application No. GB2485243 (A)—2012-05-09
[32] U.S. patent application Ser. No. 12/036,265
[33] U.S. patent application Ser. No. 12/881,285
[34] U.S. patent application Ser. No. 13/011,394

The invention claimed is:

1. A method for evaluating a hospitalized patient's risk for clinical deterioration, the method comprising:
   receiving measurements of the patient's respiratory rate, heart rate, diastolic blood pressure, and age;
   assigning, using a processor, a respiratory rate score based on a respiratory rate, a heart rate score based on the heart rate, a diastolic blood pressure score based on the diastolic blood pressure, and an age score based on the age, each score indicative of a likelihood of cardiac arrest for the patient;
   obtaining one or more regression coefficients, the one or more regression coefficients generated by performing person-time multinomial logistic regression;
   weighting the respiratory rate score, the heart rate score, the diastolic blood pressure score and the age score of the patient based on the one or more regression coefficients;
   calculating, using the processor, an aggregate score based on the patient's weighted respiratory rate score, weighted heart rate score, weighted diastolic blood pressure score, and weighted age score, the aggregate score indicative of a likelihood of cardiac arrest for the patient;
   comparing the aggregate score to a threshold to determine a level of cardiac arrest risk or clinical deterioration risk of ICU transfer or death for the patient;
   determining, based on the determined level, a treatment for the patient, wherein the treatment includes performing a rapid response team treatment, performing a critical care consult, increasing monitoring, continuing treatment, or a combination thereof; and
   sending, using the processor and based on the determined level, a notification indicating the determined level of cardiac arrest risk or clinical deterioration risk, the determined treatment, or both, for the patient to a physician, a nurse, one or more members of a rapid response team, or a combination thereof.

2. The method of claim 1, where the aggregate score is further based on data in an electronic health record corresponding to the patient, the electronic health record comprising at least one of: a respiratory rate, a blood pressure, a heart rate, an oxygen saturation, a use of supplemental oxygen, a temperature, a white cell count, a hemoglobin, a platelets, a sodium, a potassium, a chloride, a bicarbonate, an anion gap, a blood urea nitrogen, and a glucose value.

3. The method of claim 1, where the patient's respiratory rate, heart rate, systemic diastolic blood pressure and age are the only variables used to evaluate the patient's cardiac arrest risk.

4. The method of claim 3, further comprising treating the patient identified as having an aggregate score that exceeds a predetermined threshold, wherein the treating the patient included performing the rapid response team treatment, performing the critical care consult, increasing monitoring, continuing treatment, or a combination thereof.

5. The method of claim 3, where the calculating is based on performing logistic regression on one or more datasets comprising records of a plurality of patients.

6. The method of claim 5, where the calculating is based on a person-time multinomial logistic regression model and comprises separating time into discrete periods where each patient contributes a record for each period that the patient remained on wards.

7. The method of claim 1, where the aggregate score is calculated based further on the patient's quantitative mental status.

8. The method of claim 7, further comprising:
determining the patient's quantitative mental status based on the patient's answer to at least one multiple-choice question; and
where the multiple-choice question includes a query regarding at least one of: the current president, the current day, the current month, and the current year.

9. The method of claim 7, where the patient's respiratory rate, heart rate, diastolic blood pressure, age and quantitative mental status are the only variables used to evaluate the patient's cardiac arrest risk.

10. The method of claim 1, where the aggregate score is calculated based further on the patient's non-subjective mental status.

11. The method of claim 10, where the patient's respiratory rate, heart rate, diastolic blood pressure, age and non-subjective mental status are the only variables used to evaluate the patient's cardiac arrest risk.

12. The method of claim 1, where the aggregate score is calculated based further on the patient's pulse pressure.

13. The method of claim 12, where the patient's respiratory rate, heart rate, diastolic blood pressure, age and pulse pressure are the only variables used to evaluate the patient's cardiac arrest risk.

14. The method of claim 1, where the calculating and sending are automatically performed for two or more times, and further comprising generating the one or more regression coefficients based on a person-time multinomial logistic regression model of one or more hospital record datasets.

15. The method of claim 1, where the calculating and sending are automatically performed periodically, and further comprising:
updating the one or more regression coefficients based on a person-time multinomial logistic regression model of one or more hospital record datasets to generate updated regression coefficients; and
calculating, using the processor, a second aggregate score based on the updated regression coefficients.

16. A system for evaluating a hospitalized patient's risk for clinical deterioration, the system comprising:
a processor configured to:
assign a respiratory rate score based on a respiratory rate, a heart rate score based on a heart rate, a diastolic blood pressure score based on a diastolic blood pressure, and an age score based on an age, each score indicative of a likelihood of cardiac arrest for a patient;
obtaining one or more regression coefficients, the one or more regression coefficients generated by performing person-time multinomial logistic regression;
weighting the respiratory rate score, heart rate score, diastolic blood pressure score and the age score of the patient based on the one or more regression coefficients;
calculate an aggregate score based on a patient's weighted respiratory rate score, weighted heart rate score, weighted diastolic blood pressure score, and weighted age score, the aggregate score being indicative likelihood of cardiac arrest for the patient;
compare the aggregate score to a threshold to determine a level of cardiac arrest risk or clinical deterioration risk of ICU transfer or death for the patient;
determine, based on the determined level, a treatment for the patient, wherein the treatment includes performing a rapid response team treatment, performing a critical care consult, increasing monitoring, continuing treatment, or a combination thereof; and
send, based on the determined level, a notification indicating the determined level of cardiac arrest risk or clinical deterioration risk, the determined treatment, or both, for the patient to a physician, a nurse, one or more members of a rapid response team, or a combination thereof.

17. The system of claim 16, where the patient's respiratory rate, heart rate, diastolic blood pressure and age are the only variables used to evaluate the patient's cardiac arrest risk.

18. The system of claim 16, further comprising treating the patient identified as having an aggregate score that exceeds a predetermined threshold for cardiac arrest.

19. The system of claim 16, where the calculating is based on performing person-time multinomial logistic regression on one or more datasets, the one or more datasets comprising cardiac risk records of a plurality of patients.

20. The system of claim 19, where the calculating comprises separating time into discrete periods where each patient contributes a record for each period that the patient remained on wards.

21. A non-transitory computer-readable medium embodying a set of instructions executable by one or more processors, the set of instructions configured to perform a method comprising:
assigning, using a processor, a respiratory rate score based on a respiratory rate, a heart rate score based on a heart rate, a diastolic blood pressure score based on a diastolic blood pressure, and an age score based on an age, each score indicative of a likelihood of cardiac arrest for a patient;
weighting the respiratory rate score, the heart rate score, the diastolic blood pressure score and the age score of the patient by multiplying the respiratory rate score, the heart rate score, the diastolic blood pressure score and the age score by one or more regression coefficients, the one or more regression coefficients generated by performing person-time multinomial logistic regression on a data set of multiple patients;

calculating, using the processor, an aggregate score based on the patient's weighted respiratory rate score, weighted heart rate score, weighted diastolic blood pressure score, and weighted age score, the aggregate score being indicative likelihood of cardiac arrest for the patient;

comparing the aggregate score to a threshold to determine a level of cardiac arrest risk for the patient;

determining, based on the determined level, a treatment for the patient, wherein the treatment includes performing a rapid response team treatment, performing a critical care consult, increasing monitoring, continuing treatment, or a combination thereof; and sending, over a network and based on the determined level, a notification indicating the determined level of cardiac arrest risk, the determined treatment, or both, for the patient to a physician, a nurse, one or more members of a rapid response team, or a combination thereof.

22. The method of claim 1, wherein a high risk score is associated with a rapid response team or a critical care consult, and wherein a low risk score is associated with increased monitoring or continuing treatment, and wherein the clinical deterioration risk corresponds to a deterioration resulting in cardiac arrest, an intensive care unit transfer, or death.

23. The method of claim 1, further comprising adjusting a predetermined threshold based on hospital resources to generate the threshold, the predetermined threshold generated based on one or more hospital record datasets.

24. The method of claim 1, wherein weighting the respiratory rate score, the heart rate score, the diastolic blood pressure score and the age score of the patient based on the one or more regression coefficients includes weighting the respiratory rate score based on a respiratory rate logistic regression coefficient.

25. The method of claim 24, wherein the one or more regression coefficients are generated based on a person-time multinomial logistic regression model of one or more hospital record datasets.

26. The method of claim 25, wherein obtaining the one or more regression coefficients includes calculating the one or more regression coefficients by separating time into discrete periods where each prior patient of the one or more hospital record datasets contributes an input for each period that the prior patient remained in a hospital ward.

27. The method of claim 1, further comprising:
performing a mental health assessment on the patient to determine a mental health score, wherein the mental health assessment is visual sequence based; and
calculating the aggregate score further based on the patient's mental health score.

28. The method of claim 27, wherein performing a mental health assessment on the patient to determine a mental health score comprises:
presenting a first sequence of visual indicators to the patient via a display;
receiving a first input from the patient via an input device;
comparing the input to the first sequence of visual indicators;
if the first input and first the sequence of visual indicators are identical, presenting a second sequence of visual indicators having a length greater than a length of the first sequence to the patient, or
if the first input and the first sequence of visual indicators are not identical, presenting a third sequence of visual indicators having a length less than the length of the first sequence to the patient;
receiving a second input from the patient;
comparing the second input to the second sequence or the third sequence of visual indicators; and
determining the mental health score based on the first and second inputs.

29. The method of claim 1, wherein sending the notification comprises electronically transmitting the notification to an electronic device associated with the physician, the nurse, the one or more members of a rapid response team, or a combination thereof.

30. The method of claim 29, wherein the notification indicates the level of cardiac arrest risk or clinical deterioration risk of ICU transfer or death for the patient, and wherein electronically transmitting the notification comprises wirelessly transmitting the notification.

31. The method of claim 1, wherein the notification includes a score that indicates the level of cardiac arrest risk or clinical deterioration risk of ICU transfer or death for the patient.

32. The method of claim 1, wherein the notification indicates the determined treatment for the patient.

33. The method of claim 1, wherein obtaining the one or more regression coefficients includes receiving the one or more regression coefficients from another device, includes the processor retrieving the one or more regression coefficients from memory, or includes generating the one or more regression coefficients by performing person-time multinomial logistic regression on a data set of multiple patients.

34. The method of claim 1, further comprising:
updating the one or more regression coefficients by adjusting a value of at least one regression coefficient of the one or more regression coefficients based on one or more hospital record datasets.

35. The method of claim 1, wherein determining the treatment is performed after sending the notification.

* * * * *